(12) United States Patent
Lian et al.

US012318426B2

(10) Patent No.: US 12,318,426 B2
(45) Date of Patent: *Jun. 3, 2025

(54) COMPOSITIONS AND METHODS FOR THE TREATMENT OF METABOLIC AND LIVER DISORDERS

(71) Applicant: Viking Therapeutics, Inc., San Diego, CA (US)

(72) Inventors: Brian Lian, Rancho Santa Fe, CA (US); Geoffrey E. Barker, Carlsbad, CA (US); Maureen Barnes, San Diego, CA (US); Kader Yagiz, San Diego, CA (US); Erland Stevens, Davidson, NC (US)

(73) Assignee: Viking Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/774,846

(22) Filed: Jul. 16, 2024

(65) Prior Publication Data

US 2024/0366714 A1 Nov. 7, 2024

Related U.S. Application Data

(60) Continuation of application No. 18/447,990, filed on Aug. 10, 2023, which is a division of application No. 17/990,629, filed on Nov. 18, 2022, now Pat. No. 11,744,873, which is a continuation of application No. PCT/US2022/012807, filed on Jan. 18, 2022.

(60) Provisional application No. 63/139,676, filed on Jan. 20, 2021.

(51) Int. Cl.
*A61K 38/16* (2006.01)
*A61P 43/00* (2006.01)

(52) U.S. Cl.
CPC .............. *A61K 38/16* (2013.01); *A61P 43/00* (2018.01)

(58) Field of Classification Search
None
See application file for complete search history.

(56) References Cited

U.S. PATENT DOCUMENTS

| | | | |
|---|---|---|---|
| 8,835,379 B2 | 9/2014 | Nielsen et al. | |
| 9,387,176 B2 | 7/2016 | Havelund et al. | |
| 9,790,262 B2 | 10/2017 | Shandler et al. | |
| 11,744,873 B2 * | 9/2023 | Lian ..................... | C07K 14/605 514/7.2 |
| 2009/0062192 A1 | 3/2009 | Christensen et al. | |
| 2009/0318353 A1 | 12/2009 | Lau et al. | |
| 2010/0029903 A1 | 2/2010 | Conde Frieboes et al. | |
| 2010/0222269 A1 | 9/2010 | Schaffer et al. | |
| 2012/0245083 A1 | 9/2012 | Nielsen et al. | |
| 2012/0322976 A1 | 12/2012 | Wu et al. | |
| 2013/0035285 A1 | 2/2013 | Lau et al. | |
| 2013/0040877 A1 | 2/2013 | Kofoed et al. | |
| 2013/0040884 A1 | 2/2013 | Lau et al. | |
| 2013/0059781 A1 | 3/2013 | Kofoed et al. | |
| 2013/0079278 A1 | 3/2013 | Lau et al. | |
| 2013/0096055 A1 | 4/2013 | Kofoed et al. | |
| 2013/0143798 A1 | 6/2013 | Lau et al. | |
| 2013/0281363 A1 | 10/2013 | Dahl et al. | |
| 2014/0228285 A1 | 8/2014 | Hoeg-Jensen et al. | |
| 2015/0038435 A1 | 2/2015 | Hubalek | |
| 2015/0111826 A1 | 4/2015 | Riber et al. | |
| 2015/0315260 A1 | 11/2015 | Bossart et al. | |
| 2015/0322128 A1 | 11/2015 | Bossart et al. | |
| 2015/0322129 A1 | 11/2015 | Bossart et al. | |
| 2015/0374794 A1 | 12/2015 | Sensfuss et al. | |
| 2016/0102129 A1 | 4/2016 | Reedtz-Runge et al. | |
| 2016/0199438 A1 | 7/2016 | Bokvist et al. | |
| 2016/0257729 A1 | 9/2016 | Just et al. | |
| 2016/0263197 A1 | 9/2016 | Oestergaard et al. | |
| 2017/0008944 A1 | 1/2017 | Bossart et al. | |
| 2017/0112904 A1 | 4/2017 | Alsina-Fernandez et al. | |
| 2017/0114115 A1 | 4/2017 | Alsina-Fernandez et al. | |
| 2017/0137468 A1 | 5/2017 | Arata et al. | |
| 2017/0240609 A1 | 8/2017 | Shelton et al. | |
| 2017/0281788 A1 | 10/2017 | Dimarchi et al. | |
| 2017/0313750 A1 | 11/2017 | Oestergaard et al. | |
| 2018/0009871 A1 | 1/2018 | Blackwell et al. | |
| 2018/0016318 A1 | 1/2018 | Alsina-Fernandez et al. | |
| 2018/0057558 A1 | 3/2018 | Penias Navon et al. | |
| 2018/0155407 A1 | 6/2018 | Bossart et al. | |
| 2018/0162920 A1 | 6/2018 | Revell et al. | |
| 2019/0153059 A1 | 5/2019 | Hsu | |

(Continued)

FOREIGN PATENT DOCUMENTS

| | | |
|---|---|---|
| CN | 104356224 | 2/2015 |
| CN | 105753964 | 7/2016 |

(Continued)

OTHER PUBLICATIONS

Coskun et al., "LY3298176, a novel dual GIP and GLP-1 receptor agonist for the treatment of type 2 diabetes mellitus: from discovery to clinical proof of concept", Molecular Metabolism, vol. 18:3-14 (2018).
Lau et al., "Discovery of the once-weekly glucagon-like peptide-1 (GLP-1) analogue semaglutide", The Journal of Medicinal Chemistry, vol. 58:7370-7380 (2018).
International Search Report and Written Opinion for application No. PCT/US2022/012807, mailed on Apr. 11, 2022, in 11 pages.
International Preliminary Report on Patentability in application no. PCT/US2022/012807, dated Mar. 8, 2023.
Aroda et al., "A new era for oral peptides: SNAC and the development of oral semaglutide for the treatment of type 2 diabetes", Reviews in Endocrine and Metabolic Disorders, vol. 23(5):979-994 (2022).

(Continued)

*Primary Examiner* — Sudhakar Katakam
*Assistant Examiner* — Zachary J Miknis
(74) *Attorney, Agent, or Firm* — Knobbe, Martens, Olson & Bear, LLP

(57) ABSTRACT

Disclosed herein are small molecule GIP/GLP-1 dual receptor agonist compositions, pharmaceutical compositions, the use and preparation thereof.

22 Claims, No Drawings

Specification includes a Sequence Listing.

(56) References Cited

U.S. PATENT DOCUMENTS

| | | |
|---|---|---|
| 2019/0194285 A1 | 6/2019 | Olsen et al. |
| 2019/0233493 A1 | 8/2019 | Brasseur et al. |
| 2019/0233494 A1 | 8/2019 | Duclos et al. |
| 2019/0309040 A1 | 10/2019 | Thennati et al. |
| 2019/0338008 A1 | 11/2019 | Palani et al. |
| 2019/0345529 A1 | 11/2019 | Nuijens et al. |
| 2019/0388502 A1 | 12/2019 | Corvari et al. |
| 2020/0023040 A1 | 1/2020 | Benson et al. |
| 2020/0024322 A1 | 1/2020 | Abraham et al. |
| 2020/0140514 A1 | 5/2020 | Briere et al. |
| 2020/0155487 A1 | 5/2020 | Choi et al. |
| 2020/0155650 A1 | 5/2020 | Choi et al. |
| 2020/0270325 A1 | 8/2020 | Palani et al. |
| 2020/0317721 A1 | 10/2020 | Barlos et al. |
| 2020/0331980 A1 | 10/2020 | Alsina-Fernandez et al. |
| 2021/0009631 A1 | 1/2021 | Schonleber et al. |
| 2021/0100911 A1 | 4/2021 | Mrsny et al. |
| 2021/0284694 A1 | 9/2021 | Ricardo et al. |
| 2021/0338781 A1 | 11/2021 | Benson et al. |
| 2021/0355186 A1 | 11/2021 | Brown et al. |
| 2022/0016215 A1 | 1/2022 | Takekawa et al. |
| 2022/0016254 A1 | 1/2022 | Wu et al. |
| 2022/0017589 A1 | 1/2022 | Zhang et al. |
| 2022/0025010 A1 | 1/2022 | Sparre-Ulrich et al. |
| 2022/0025116 A1 | 1/2022 | Pae et al. |
| 2022/0041678 A1 | 2/2022 | Haebel et al. |
| 2022/0041680 A1 | 2/2022 | Incisivo et al. |
| 2022/0047678 A1 | 2/2022 | Djedjos et al. |
| 2022/0133856 A1 | 5/2022 | Zhang et al. |
| 2022/0135639 A1 | 5/2022 | Coffin et al. |
| 2022/0193245 A1 | 6/2022 | Coskun et al. |
| 2022/0204580 A1 | 6/2022 | Bednarek et al. |
| 2022/0273762 A1 | 9/2022 | Corvari et al. |
| 2022/0275029 A1 | 9/2022 | Mrsny et al. |
| 2022/0288168 A1 | 9/2022 | Abraham et al. |
| 2022/0306695 A1 | 9/2022 | Shelton et al. |
| 2024/0058415 A1 * | 2/2024 | Lian .................... C07K 14/605 |
| 2024/0239843 A1 | 7/2024 | Lian et al. |

FOREIGN PATENT DOCUMENTS

| | | | | |
|---|---|---|---|---|
| CN | 106478806 | 3/2017 | | |
| CN | 106749613 | 5/2017 | | |
| CN | 108359005 | 8/2018 | | |
| CN | 108676087 | 10/2018 | | |
| CN | 109021092 | 12/2018 | | |
| CN | 109456402 | 3/2019 | | |
| CN | 110642935 | 1/2020 | | |
| CN | 110684082 | 1/2020 | | |
| CN | 110903355 | 3/2020 | | |
| CN | 111116731 | 5/2020 | | |
| CN | 111234015 | 6/2020 | | |
| CN | 111320683 | 6/2020 | | |
| CN | 111718407 | 9/2020 | | |
| CN | 111732650 | 10/2020 | | |
| CN | 112110981 | 12/2020 | | |
| CN | 112592387 | 4/2021 | | |
| CN | 112661815 | 4/2021 | | |
| CN | 113045641 | 6/2021 | | |
| CN | 113583106 | 11/2021 | | |
| CN | 113637064 | 11/2021 | | |
| CN | 113754753 | 12/2021 | | |
| CN | 113880935 | 1/2022 | | |
| CN | 114031680 | 2/2022 | | |
| CN | 114249810 | 3/2022 | | |
| CN | 114736271 | 7/2022 | | |
| CN | 114949183 | 8/2022 | | |
| CN | 115160429 | 10/2022 | | |
| CN | 115181173 | 10/2022 | | |
| CN | 115181174 | 10/2022 | | |
| CN | 115368452 | 11/2022 | | |
| CN | 115594752 | 1/2023 | | |
| CN | 115651075 | 1/2023 | | |
| CN | 115677827 | 2/2023 | | |
| CN | 115806593 | 3/2023 | | |
| CN | 115991742 | 4/2023 | | |
| CN | 116023444 | 4/2023 | | |
| CN | 116120403 | 5/2023 | | |
| CN | 116120425 | 5/2023 | | |
| CN | 116178523 | 5/2023 | | |
| CN | 116355041 | 6/2023 | | |
| CN | 116693629 | 9/2023 | | |
| CN | 116854805 | 10/2023 | | |
| EA | 031591 | 1/2019 | | |
| EP | 3398961 | 11/2018 | | |
| EP | 3819308 | 5/2021 | | |
| EP | 4043026 | 8/2022 | | |
| EP | 4043480 | 8/2022 | | |
| EP | 4159750 | 4/2023 | | |
| EP | 4230640 | 8/2023 | | |
| JP | 2017-529354 | 10/2017 | | |
| JP | 2023-541806 | 10/2023 | | |
| WO | WO 2008/145721 | 12/2008 | | |
| WO | WO 2011/117415 | 9/2011 | | |
| WO | WO 2012/138941 | 10/2012 | | |
| WO | WO 2013/164483 | 11/2013 | | |
| WO | WO 2015/067715 | 5/2015 | | |
| WO | WO 2015/067716 | 5/2015 | | |
| WO | WO 2016/066744 | 5/2016 | | |
| WO | WO 2016/111971 | 7/2016 | | |
| WO | WO 2016/124687 | 8/2016 | | |
| WO | WO 2017/075522 | 5/2017 | | |
| WO | WO 2017/149070 | 9/2017 | | |
| WO | WO 2017/211922 | 12/2017 | | |
| WO | WO 2018/032843 | 2/2018 | | |
| WO | WO 2018/103868 | 6/2018 | | |
| WO | WO 2019/034726 | 2/2019 | | |
| WO | WO 2019/140025 | 7/2019 | | |
| WO | WO 2019/140030 | 7/2019 | | |
| WO | WO 2019/166411 | 9/2019 | | |
| WO | WO 2019/183577 | 9/2019 | | |
| WO | WO 2019/207427 | 10/2019 | | |
| WO | WO 2019/229242 | 12/2019 | | |
| WO | WO 2019/245893 | 12/2019 | | |
| WO | WO 2020/023382 | 1/2020 | | |
| WO | WO 2020/039051 | 2/2020 | | |
| WO | WO 2020/067575 | 4/2020 | | |
| WO | WO 2020/134717 | 7/2020 | | |
| WO | WO 2020/159949 | 8/2020 | | |
| WO | WO-2020159949 A1 * | 8/2020 | ............ | A61K 38/00 |
| WO | WO 2020/190757 | 9/2020 | | |
| WO | WO 2021/021877 | 2/2021 | | |
| WO | WO 2021/034815 | 2/2021 | | |
| WO | WO 2021/044287 | 3/2021 | | |
| WO | WO 2021/066600 | 4/2021 | | |
| WO | WO 2021/070202 | 4/2021 | | |
| WO | WO 2021/126695 | 6/2021 | | |
| WO | WO 2021/127466 | 6/2021 | | |
| WO | WO 2021/136223 | 7/2021 | | |
| WO | WO 2021/136296 | 7/2021 | | |
| WO | WO 2021/136303 | 7/2021 | | |
| WO | WO 2021/139744 | 7/2021 | | |
| WO | WO 2021/143073 | 7/2021 | | |
| WO | WO 2021/150673 | 7/2021 | | |
| WO | WO 2021/154593 | 8/2021 | | |
| WO | WO 2021/158444 | 8/2021 | | |
| WO | WO 2021/160185 | 8/2021 | | |
| WO | WO 2021/163972 | 8/2021 | | |
| WO | WO 2021/164663 | 8/2021 | | |
| WO | WO 2021/175974 | 9/2021 | | |
| WO | WO 2021/205388 | 10/2021 | | |
| WO | WO 2021/224938 | 11/2021 | | |
| WO | WO 2021/227989 | 11/2021 | | |
| WO | WO 2021/239082 | 12/2021 | | |
| WO | WO 2021/242756 | 12/2021 | | |
| WO | WO 2021/252931 | 12/2021 | | |
| WO | WO 2021/260530 | 12/2021 | | |
| WO | WO 2022/007805 | 1/2022 | | |
| WO | WO 2022/007809 | 1/2022 | | |
| WO | WO 2022/013374 | 1/2022 | | |
| WO | WO 2022/023723 | 2/2022 | | |
| WO | WO 2022/026629 | 2/2022 | | |
| WO | WO 2022/026633 | 2/2022 | | |
| WO | WO 2022/033047 | 2/2022 | | |

(56) References Cited

FOREIGN PATENT DOCUMENTS

| | | |
|---|---|---|
| WO | WO 2022/037470 | 2/2022 |
| WO | WO 2022/038179 | 2/2022 |
| WO | WO 2022/079639 | 4/2022 |
| WO | WO 2022/080986 | 4/2022 |
| WO | WO 2022/090447 | 5/2022 |
| WO | WO 2022/096736 | 5/2022 |
| WO | WO 2022/115799 | 6/2022 |
| WO | WO 2022/117044 | 6/2022 |
| WO | WO 2022/117056 | 6/2022 |
| WO | WO 2022/129526 | 6/2022 |
| WO | WO 2022/133148 | 6/2022 |
| WO | WO 2022/133797 | 6/2022 |
| WO | WO 2022/134124 | 6/2022 |
| WO | WO 2022/159395 | 7/2022 |
| WO | WO 2022/177742 | 8/2022 |
| WO | WO 2022/177878 | 8/2022 |
| WO | WO 2022/178366 | 8/2022 |
| WO | WO 2022/199629 | 9/2022 |
| WO | WO 2022/241287 | 11/2022 |
| WO | WO 2022/247950 | 12/2022 |
| WO | WO 2022/271611 | 12/2022 |
| WO | WO 2022/272019 | 12/2022 |
| WO | WO 2023/028466 | 3/2023 |
| WO | WO 2023/044290 | 3/2023 |
| WO | WO 2023/086499 | 5/2023 |
| WO | WO 2023/089594 | 5/2023 |
| WO | WO 2023/141044 | 7/2023 |
| WO | WO 2023/161939 | 8/2023 |
| WO | WO 2023/174433 | 9/2023 |
| WO | WO 2024/020372 | 1/2024 |
| WO | WO 2024/020388 | 1/2024 |
| WO | WO 2024/107862 | 5/2024 |
| WO | WO 2024/192219 | 9/2024 |

OTHER PUBLICATIONS

Ismail et al., "Encapsulation in plymeric nanoparticles enhances the enzymatic stability and the permeability of the GLP-1 analog, liraglutide, across a culture model of intestinal permeability", Pharmaceutics, vol. 11(11):599 (2019).

Knudsen et al., "The discovery and development of liraglutide and semaglutide", Frontiers in Endocrinology, vol. 10:440904 (2019).

Lassalas et al., "Structure property relationships of carboylic acid isosteres", Journal of Medicinal Chemistry, vol. 59:3183-3203 (2016).

Maher et al., "Overcoming poor permeability: translating permeation enhancers for oral peptide delivery", Drug Discovery Today: Technologies, vol. 9(2):e113-e119 (2012).

Pechenov et al., "Development of an orally delivered GLP-1 receptor agonist through peptide engineering and drug delivery to treat chronic disease", Scientific Reports, vol. 11(1):22521 (2021).

Maag et al., "Prodrugs of Carboxylic Acids", Biotechnology Pharmaceutical Aspects, vol. V:703-729, Springer NY (2007).

* cited by examiner

COMPOSITIONS AND METHODS FOR THE TREATMENT OF METABOLIC AND LIVER DISORDERS

CROSS REFERENCE TO RELATED APPLICATIONS

This application is a continuation of U.S. application Ser. No. 18/447,990, filed Aug. 10, 2023, which is a division of U.S. application Ser. No. 17/990,628, filed Nov. 18, 2022, now U.S. Pat. No. 11,744,873, which is a continuation of International Application No. PCT/US2022/012807, filed Jan. 18, 2022, which claims the benefit of U.S. Provisional Application No. 63/139,676, filed Jan. 20, 2021, each of which is incorporated herein by reference in its entirety.

REFERENCE TO SEQUENCE LISTING

The present application is being filed along with a Sequence Listing in electronic format. The Sequence Listing is provided as a file entitled VIKNG.016C2.xml, created on Jul. 15, 2024, which is 4 kilobytes in size. The information in the electronic format of the Sequence Listing is incorporated herein by reference in its entirety.

BACKGROUND

Field of the Invention

The present disclosure relates generally to the field of treatments for metabolic disorders and fatty liver diseases. More specifically, the present disclosure relates to the field of small molecule drugs for the treatment of non-alcoholic steatohepatitis (NASH), non-alcoholic fatty liver disease (NAFLD).

Description of the Related Art

Incretin peptides glucose-dependent insulinotropic polypeptide (GIP) and glucagon-like peptide-1 (GLP-1) are metabolic hormones. GIP and GLP-1 are both secreted within minutes of nutrient ingestion and facilitate the rapid disposal of ingested nutrients. Both peptides share common actions on islet β-cells acting through structurally distinct yet related receptors. Incretin-receptor activation leads to glucose-dependent insulin secretion, induction of 3-cell proliferation, and enhanced resistance to apoptosis. GIP also promotes energy storage via direct actions on adipose tissue. In contrast, GLP-1 exerts glucoregulatory actions via slowing of gastric emptying and glucose-dependent inhibition of glucagon secretion. GLP-1 also promotes satiety and sustained GLP-1-receptor activation is associated with weight loss in both preclinical and clinical studies.

Non-alcoholic fatty liver disease (NAFLD) is the hepatic manifestation of metabolic syndrome and is the most common cause of chronic liver disease. NAFLD may progress to liver inflammation, fibrosis, cirrhosis and even hepatocellular carcinoma. GIP/GLP-1 dual receptor agonists have been developed for treating NAFLD, non-alcoholic steatohepatitis (NASH), diabetes, obesity, and other diseases. However, the use of GIP/GLP-1 dual receptor agonists is associated with nausea, vomiting, and/or diarrhea. For example, clinical trials of a GIP/GLP1 dual receptor agonist compound found that tolerability at high doses was limited by gastrointestinal adverse events. The dose limitation associated with gastrointestinal adverse events may prevent dosing to the desired effective dose, may compromise patient compliance with treatment, and may limit the effectiveness of the treatment regimen. Therefore, a need exists for novel GIP/GLP1 dual agonist compounds that can be used to treat fatty liver diseases and other diseases and disorders.

SUMMARY

Some embodiments disclosed herein include a compound having the structure of the formula I:

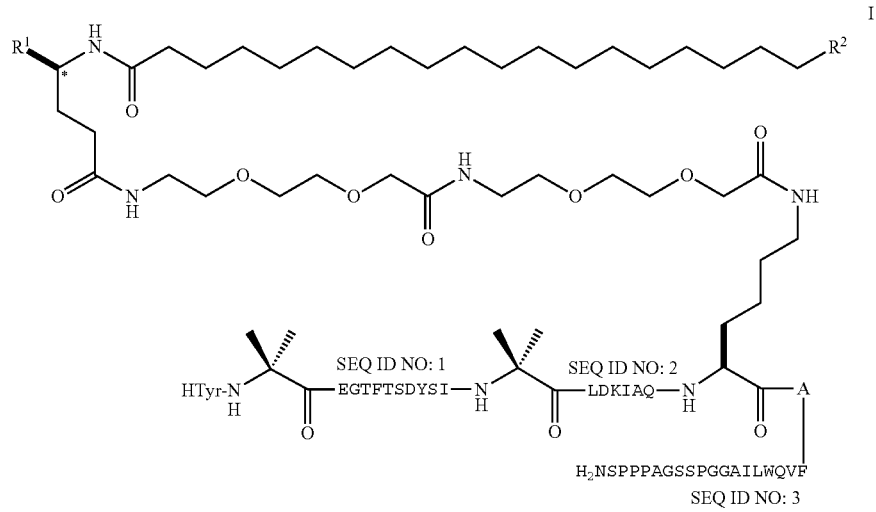

or a pharmaceutically acceptable salt thereof, wherein:

$R^1$ is selected from the group consisting of —C(=O)(OZ$^1$), —P(=O)(X)(Y) and a 5-10 membered heteroaryl containing 1-2 heteroatoms selected from N, O and S optionally substituted with 1-2 $R^7$ independently selected from halogen, $C_{1-6}$ alkyl, halo$C_{1-6}$ alkyl, halo$C_{1-6}$ alkoxy, —OR$^5$, $C_{3-10}$ cycloalkyl, $C_{6-10}$ aryl, 5-10 membered heteroaryl and 5-10 membered heterocyclyl;

$R^2$ is selected from the group consisting of —C(=O)(OZ$^2$), —P(=O)(X)(Y) and a 5-10 membered heteroaryl containing 1-2 heteroatoms selected from N, O and S optionally substituted with 1-2 $R^7$ independently selected from halogen, $C_{1-6}$ alkyl, halo$C_{1-6}$ alkyl, halo$C_{1-6}$ alkoxy, —OR$^5$, $C_{3-10}$ cycloalkyl, $C_{6-10}$ aryl, 5-10 membered heteroaryl and 5-10 membered heterocyclyl;

each $R^7$ may be independently selected from the group consisting of halogen, $C_{1-6}$ alkyl, halo$C_{1-6}$ alkyl, halo$C_{1-6}$ alkoxy, $C_{1-6}$ alkoxy, $C_{3-10}$ cycloalkyl, $C_{6-10}$ aryl, 5-10 membered heteroaryl and 5-10 membered heterocyclyl;

X and Y may each be independently selected from the group consisting of —OR$^4$, NR$^5$R$^6$, $C_{1-6}$ alkyl and halo$C_{1-6}$ alkyl;

each $R^4$ may be independently selected from the group consisting of hydrogen, $C_{1-6}$ alkyl, halo$C_{1-6}$ alkyl, $C_{6-10}$ aryloxy and $C_{6-10}$ aryl alkoxy;

each $R^5$ may be independently hydrogen or $C_{1-6}$ alkyl;

each $R^6$ may be independently hydrogen or $C_{1-6}$ alkyl; and $Z^1$ and $Z^2$ may each be independently selected from the group consisting of hydrogen, $C_{1-6}$ alkyl, halo$C_{1-6}$ alkyl, halo$C_{1-6}$ alkoxy, $C_{1-6}$ alkoxy, $C_{3-10}$ cycloalkyl and $C_{6-10}$ aryl, with the provisio that at least one of $Z^1$ and $Z^2$ is not hydrogen.

Other embodiments disclosed herein include a pharmaceutical composition comprising a therapeutically effective amount of a compound disclosed herein and a pharmaceutically acceptable excipient.

Other embodiments disclosed herein include a method of preventing, treating, or ameliorating one or more fatty liver diseases in a subject, by administering the compounds disclosed herein, or a pharmaceutically acceptable salt thereof, to a subject in need thereof. The fatty liver diseases include but are not limited to steatosis, non-alcoholic steatohepatitis (NASH), non-alcoholic fatty liver disease (NAFLD).

Other embodiments disclosed herein include a method of preventing, treating, or ameliorating one or disease or disorders in a subject, by administering the compounds disclosed herein, or a pharmaceutically acceptable salt thereof, to a subject in need thereof. In some embodiments, said disease or disorder is liver fibrosis, renal fibrosis, biliary fibrosis, pancreatic fibrosis, nonalcoholic steatohepatitis, non-alcoholic fatty liver disease, chronic kidney disease, diabetic kidney disease, primary sclerosing cholangitis, primary biliary cirrhosis, or idiopathic fibrosis. In some embodiments, said disease or disorder is a metabolic disorder or a metabolic syndrome. In some embodiments, said disease or disorder is atherosclerosis, diabetes, hyperglycemic diabetes, type 2 diabetes mellitus, dyslipidemia, hypercholesterolemia, hyperlipidemia, hypertension, hypoglycemia, obesity, or prader-willi syndrome.

DETAILED DESCRIPTION

In some embodiments, compounds that are non-macrocyclic functionalized peptides are provided that act as GIP/GLP-1 dual receptor agonists. Various embodiments of these compounds include compounds having the structure of formula I as described above or pharmaceutically acceptable salts thereof. The structure of formula I encompasses all stereoisomers and racemic mixtures, including the following structure and mixtures thereof:

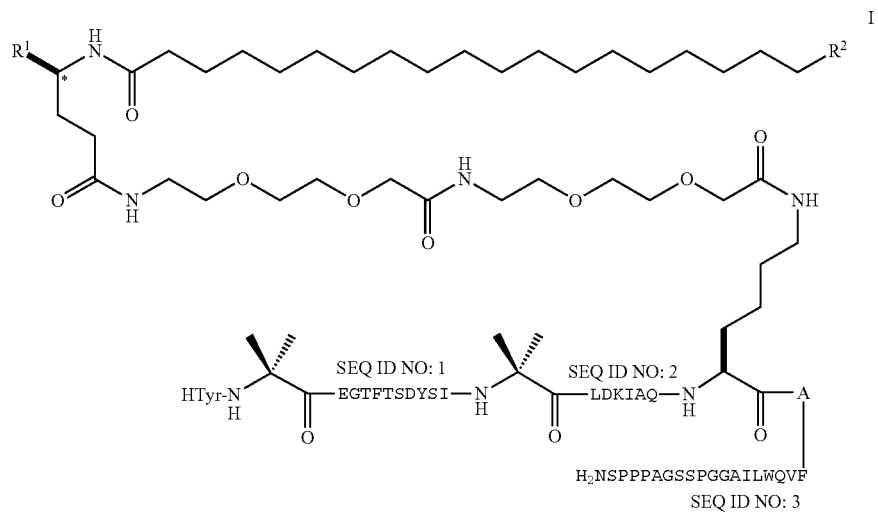

In some embodiments of compounds of formula I:

$R^1$ is selected from the group consisting of —C(=O)(OZ$^1$), —P(=O)(X)(Y) and a 5-10 membered heteroaryl containing 1-2 heteroatoms selected from N, O and S optionally substituted with 1-2 $R^7$ independently selected from halogen, $C_{1-6}$ alkyl, haloC$_{1-6}$ alkyl, haloC$_{1-6}$ alkoxy, —OR$^5$, $C_{3-10}$ cycloalkyl, $C_{6-10}$ aryl, 5-10 membered heteroaryl and 5-10 membered heterocyclyl;

$R^2$ is selected from the group consisting of —C(=O)(OZ$^2$), —P(=O)(X)(Y) and a 5-10 membered heteroaryl containing 1-2 heteroatoms selected from N, O and S optionally substituted with 1-2 $R^7$ independently selected from halogen, $C_{1-6}$ alkyl, haloC$_{1-6}$ alkyl, haloC$_{1-6}$ alkoxy, —OR$^5$, $C_{3-10}$ cycloalkyl, $C_{6-10}$ aryl, 5-10 membered heteroaryl and 5-10 membered heterocyclyl;

each $R^7$ may be independently selected from the group consisting of halogen, $C_{1-6}$ alkyl, haloC$_{1-6}$ alkyl, haloC$_{1-6}$ alkoxy, $C_{1-6}$ alkoxy, $C_{3-10}$ cycloalkyl, $C_{6-10}$ aryl, 5-10 membered heteroaryl and 5-10 membered heterocyclyl;

X and Y may each be independently selected from the group consisting of —OR$^4$, NR$^5$R$^6$, $C_{1-6}$ alkyl and haloC$_{1-6}$ alkyl;

each $R^4$ may be independently selected from the group consisting of hydrogen, $C_{1-6}$ alkyl, haloC$_{1-6}$ alkyl, $C_{6-10}$ aryloxy and $C_{6-10}$ aryl alkoxy;

each $R^5$ may be independently hydrogen or $C_{1-6}$ alkyl;

each $R^6$ may be independently hydrogen or $C_{1-6}$ alkyl; and $Z^1$ and $Z^2$ may each be independently selected from the group consisting of hydrogen, $C_{1-6}$ alkyl, haloC$_{1-6}$ alkyl, haloC$_{1-6}$ alkoxy, $C_{1-6}$ alkoxy, $C_{3-10}$ cycloalkyl and $C_{6-10}$ aryl, with the provisio that at least one of $Z^1$ and $Z^2$ is not hydrogen.

Some embodiments of compounds of formula I include compounds having the structure of formula I-a:

In some embodiments of compounds of formula I-a or their pharmaceutically acceptable salts; $Z^1$ is selected from hydrogen, $C_{1-6}$ alkyl, haloC$_{1-6}$ alkyl, haloC$_{1-6}$ alkoxy, $C_{1-6}$ alkoxy, $C_{3-10}$ cycloalkyl and $C_{6-10}$ aryl; and X and Y each are —OR$^4$.

In some embodiments of compounds of formula I-a or their pharmaceutically acceptable salts; $Z^1$ is selected from hydrogen, haloC$_{1-6}$ alkoxy and $C_{1-6}$ alkoxy; and each $R^4$ may be independently selected from hydrogen, $C_{6-10}$ aryloxy and $C_{6-10}$ aryl alkoxy.

In some embodiments of compounds of formula I-a or their pharmaceutically acceptable salts; $Z^1$ is hydrogen and each $R^4$ may be independently hydrogen or $C_{6-10}$ aryl alkoxy.

In some embodiments of compounds of formula I-a or their pharmaceutically acceptable salts; each $R^4$ is hydrogen.

In some embodiments of compounds of formula I-a or their pharmaceutically acceptable salts; $Z^1$ is hydrogen and each $R^4$ is hydrogen.

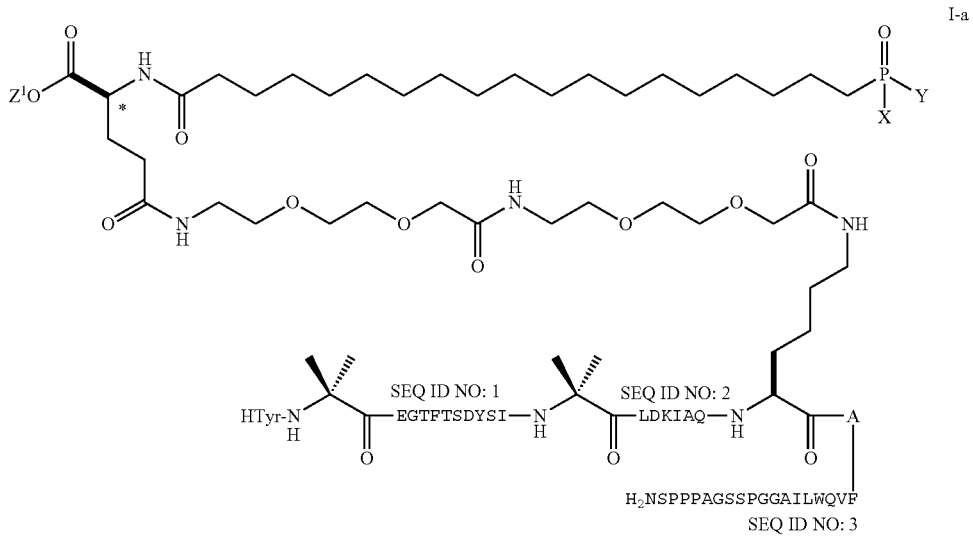

I-a or pharmaceutically acceptable salts thereof.

Some embodiments of compounds of formula I include compounds having the structure of formula I-b:

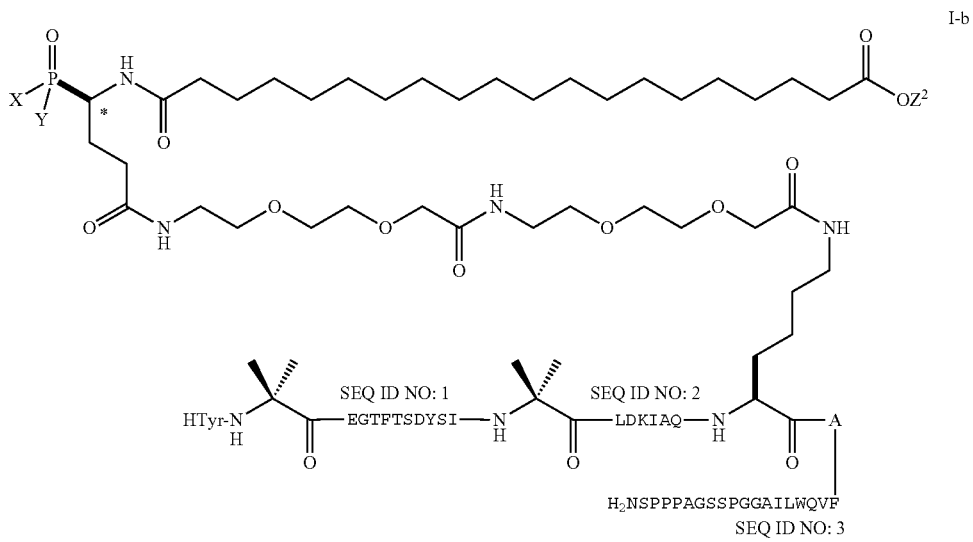

I-b or pharmaceutically acceptable salts thereof.

In some embodiments of compounds of formula I-b or their pharmaceutically acceptable salts; $Z^2$ is selected from hydrogen, $C_{1-6}$ alkyl, haloC$_{1-6}$ alkyl, haloC$_{1-6}$ alkoxy, $C_{1-6}$ alkoxy, $C_{3-10}$ cycloalkyl and $C_{6-10}$ aryl; and X and Y each are —OR$^4$.

In some embodiments of compounds of formula I-b or their pharmaceutically acceptable salts; $Z^2$ is selected from hydrogen, haloC$_{1-6}$ alkoxy and $C_{1-6}$ alkoxy; and each $R^4$ may be independently selected from hydrogen, $C_{6-10}$ aryloxy and $C_{6-10}$ aryl alkoxy.

In some embodiments of compounds of formula I-b or their pharmaceutically acceptable salts; $Z^2$ is hydrogen and each $R^4$ may be independently hydrogen or $C_{6-10}$ aryl alkoxy.

In some embodiments of compounds of formula I-b or their pharmaceutically acceptable salts; each $R^4$ is hydrogen.

In some embodiments of compounds of formula I-b or their pharmaceutically acceptable salts; $Z^2$ is hydrogen and each $R^4$ is hydrogen.

Some embodiments of compounds of formula I include compounds having the structure of formula I-c:

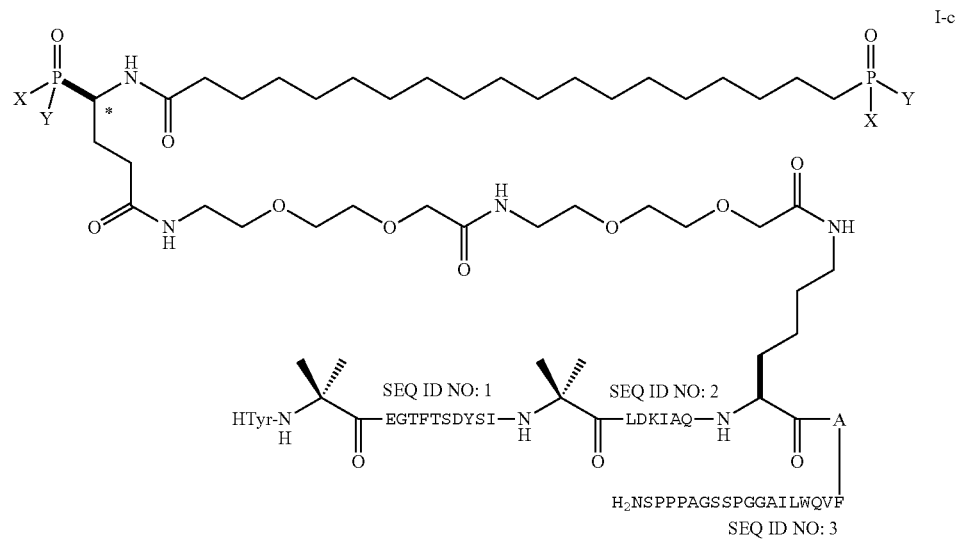

I-c or pharmaceutically acceptable salts thereof.

In some embodiments of compounds of formula I-c or their pharmaceutically acceptable salts; X and Y each are —OR$^4$.

In some embodiments of compounds of formula I-c or their pharmaceutically acceptable salts; each $R^4$ may be independently selected from hydrogen, $C_{6-10}$ aryloxy and $C_{6-10}$ aryl alkoxy.

In some embodiments of compounds of formula I-c or their pharmaceutically acceptable salts; each $R^4$ is hydrogen.
Some embodiments include a compound having the structure selected from the group consisting of:
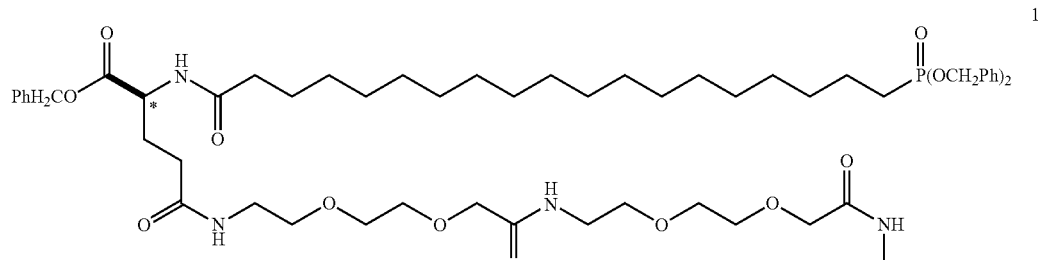
1
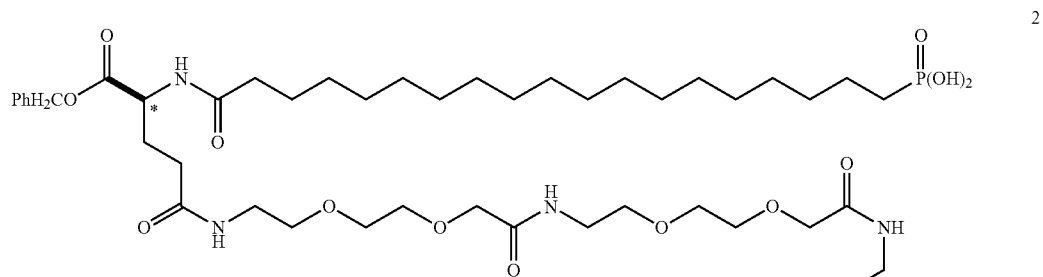
2
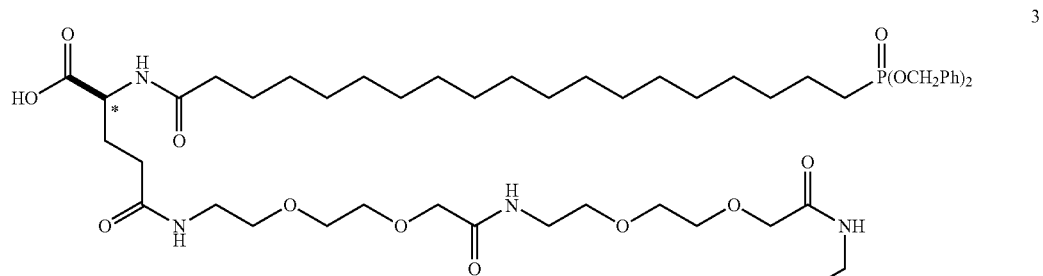
3

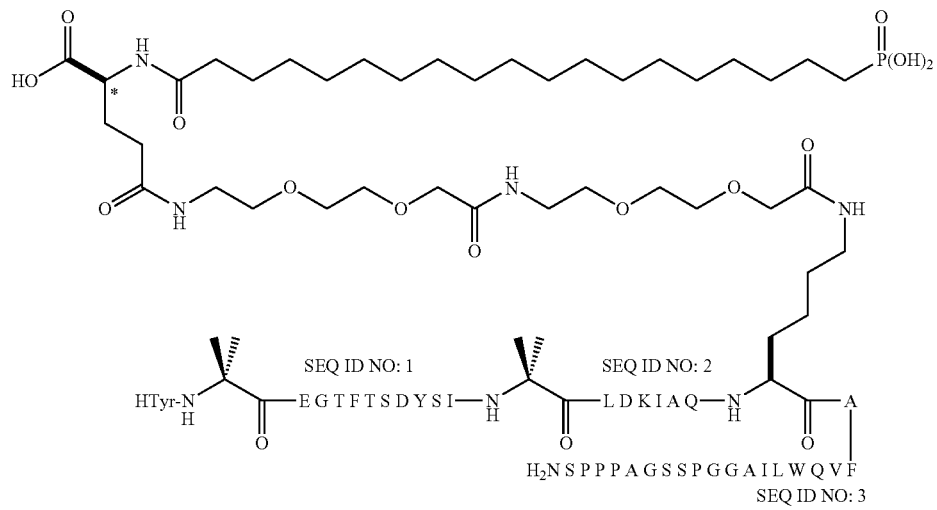
4
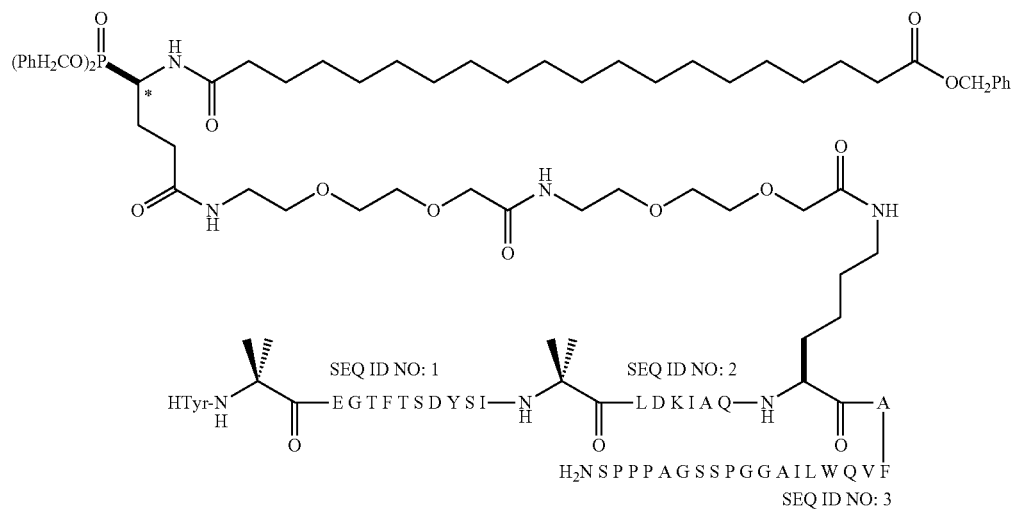
5
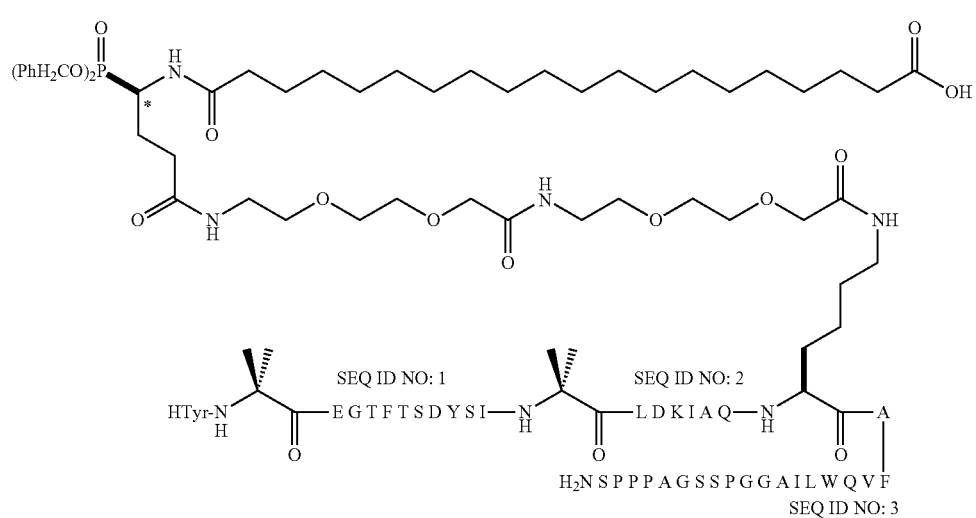
6

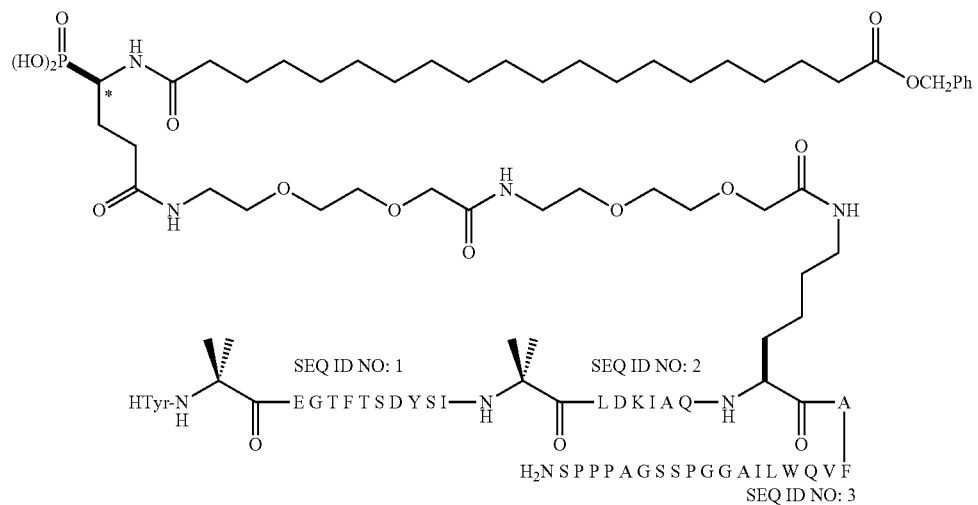
7
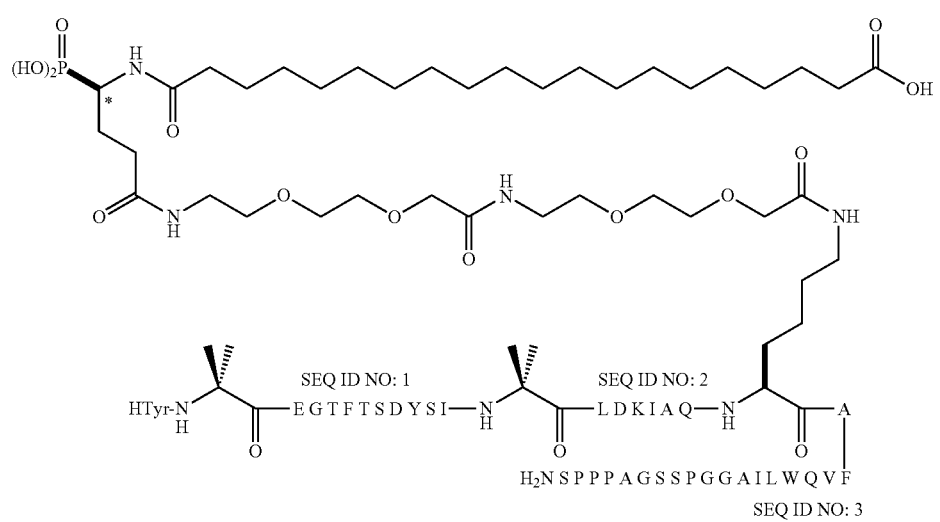
8
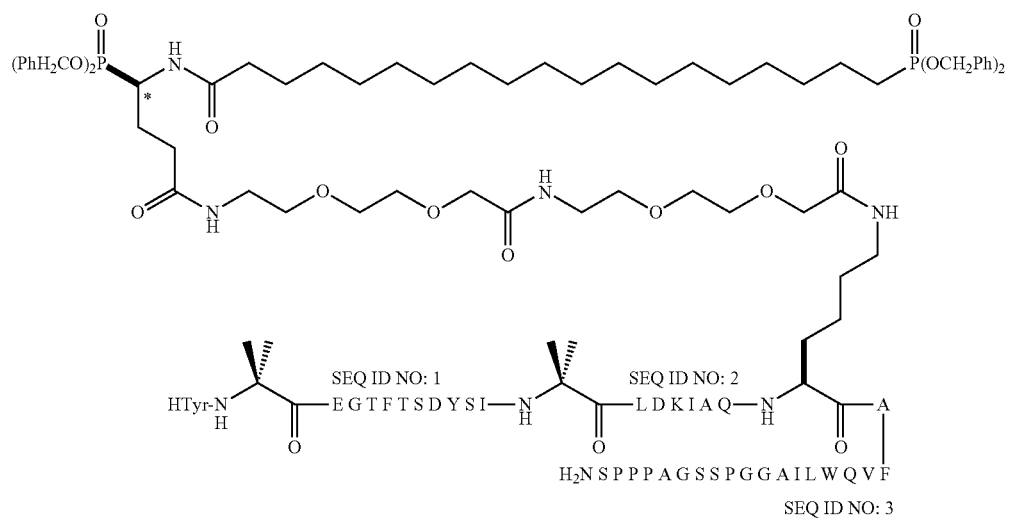
9

-continued
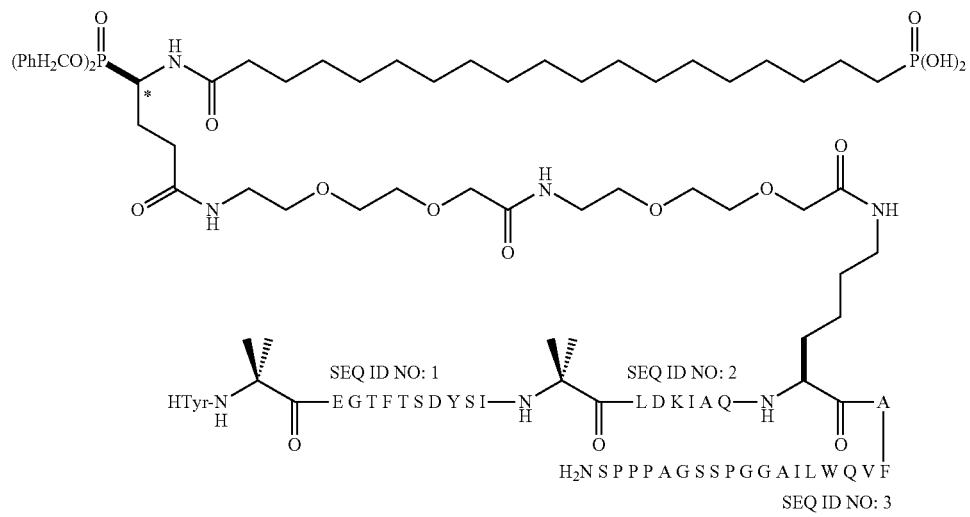
10
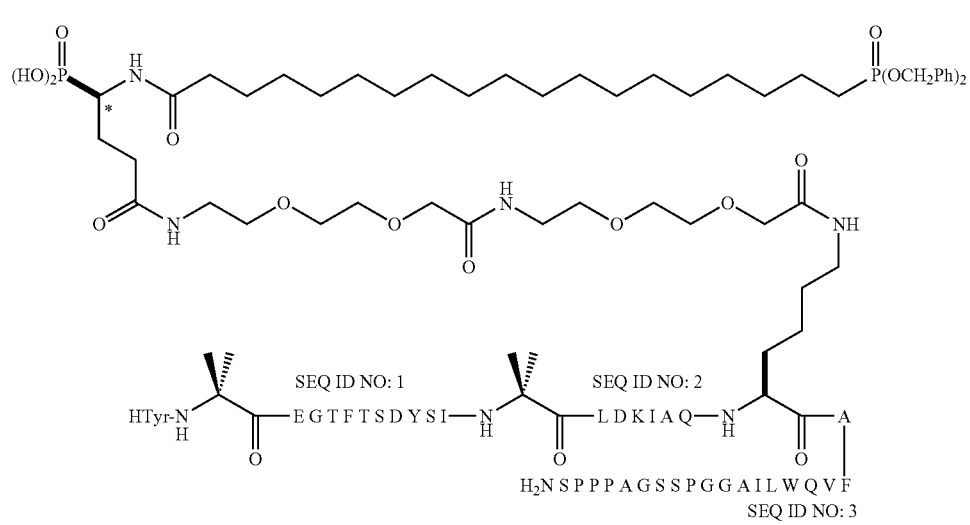
11
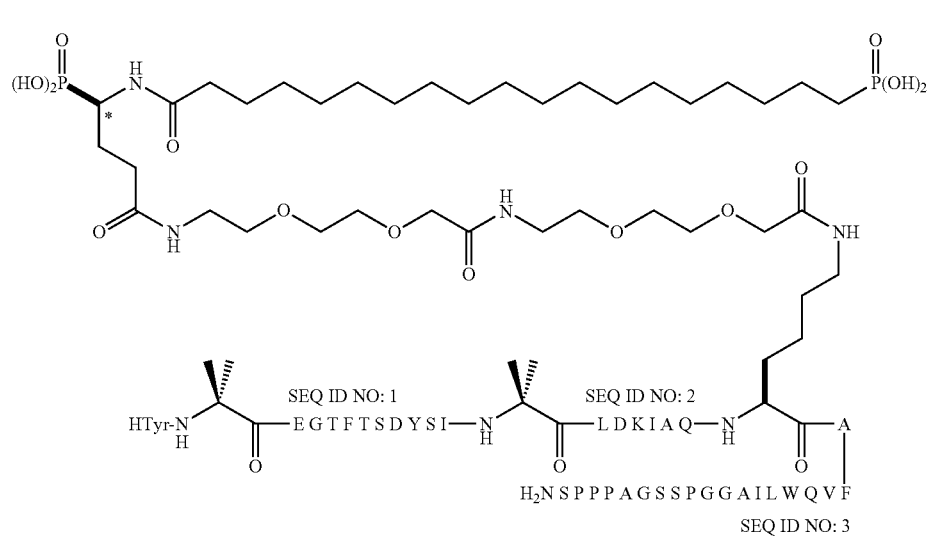
12
and pharmaceutically acceptable salts thereof.

Some embodiments include a compound wherein "*" indicates a chiral carbon with "S" configuration.

Some embodiments include a compound wherein "*" indicates a chiral carbon with "R" configuration.

Where the compounds disclosed herein have at least one chiral center, they may exist as individual enantiomers and diastereomers or as mixtures of such isomers, including racemates. Separation of the individual isomers or selective synthesis of the individual isomers is accomplished by application of various methods which are well known to practitioners in the art. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

"Solvate" refers to the compound formed by the interaction of a solvent and a compound described herein or salt thereof. Suitable solvates are pharmaceutically acceptable solvates including hydrates.

The term "pharmaceutically acceptable salt" refers to salts that retain the biological effectiveness and properties of a compound, which are not biologically or otherwise undesirable for use in a pharmaceutical. In many cases, the compounds herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means any one of the radio-stable atoms of column 7 of the Periodic Table of the Elements, e.g., fluorine, chlorine, bromine, or iodine, with fluorine and chlorine being preferred.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group of the compounds may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, isopropyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "haloalkyl" refers to a straight- or branched-chain alkyl group having from 1 to 12 carbon atoms in the chain, substituting one or more hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$ and other groups that in light of the ordinary skill in the art and the teachings provided herein, would be considered equivalent to any one of the foregoing examples.

As used herein, "alkoxy" refers to the formula —OR wherein R is an alkyl as is defined above, such as "$C_{1-9}$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "polyethylene glycol" refers to the formula

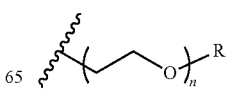

wherein n is an integer greater than one and R is a hydrogen or alkyl. The number of repeat units "n" may be indicated by referring to a number of members. Thus, for example, "2- to 5-membered polyethylene glycol" refers to n being an integer selected from two to five. In some embodiments, R is selected from methoxy, ethoxy, n-propoxy, 1-methylethoxy (isopropoxy), n-butoxy, iso-butoxy, sec-butoxy, and tert-butoxy.

As used herein, "heteroalkyl" refers to a straight or branched hydrocarbon chain containing one or more heteroatoms, that is, an element other than carbon, including but not limited to, nitrogen, oxygen and sulfur, in the chain backbone. The heteroalkyl group may have 1 to 20 carbon atoms although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. In various embodiments, the heteroalkyl may have from 1 to 4 heteroatoms, from 1 to 3 heteroatoms, 1 or 2 heteroatoms, or 1 heteroatom. The heteroalkyl group of the compounds may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "aryloxy" and "arylthio" refers to RO- and RS-, in which R is an aryl as is defined above, such as "$C_{6-10}$ aryloxy" or "$C_{6-10}$ arylthio" and the like, including but not limited to phenyloxy.

An "aralkyl" or "arylalkyl" is an aryl group connected, as a substituent, via an alkylene group, such "$C_{7-14}$ aralkyl" and the like, including but not limited to benzyl, 2-phenylethyl, 3-phenylpropyl, and naphthylalkyl. In some cases, the alkylene group is a lower alkylene group (i.e., a $C_{1-4}$ alkylene group).

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. In various embodiments, a heteroaryl contains from 1 to 4 heteroatoms, from 1 to 3 heteroatoms, from 1 to 2 heteroatoms, or 1 heteroatom. For example, in various embodiments, a heteroaryl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

A "heteroaralkyl" or "heteroarylalkyl" is heteroaryl group connected, as a substituent, via an alkylene group. Examples include but are not limited to 2-thienylmethyl, 3-thienylmethyl, furylmethyl, thienylethyl, pyrrolylalkyl, pyridylalkyl, isoxazollylalkyl, and imidazolylalkyl. In some cases, the alkylene group is a lower alkylene group (i.e., a $C_{1-4}$ alkylene group).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl.

A "(carbocyclyl)alkyl" is a carbocyclyl group connected, as a substituent, via an alkylene group, such as "$C_{4-10}$ (carbocyclyl)alkyl" and the like, including but not limited to, cyclopropylmethyl, cyclobutylmethyl, cyclopropylethyl, cyclopropylbutyl, cyclobutylethyl, cyclopropylisopropyl, cyclopentylmethyl, cyclopentylethyl, cyclohexylmethyl, cyclohexylethyl, cycloheptylmethyl, and the like. In some cases, the alkylene group is a lower alkylene group.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" means a carbocyclyl ring or ring system having at least one double bond, wherein no ring in the ring system is aromatic. An example is cyclohexenyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations.

In various embodiments, a heterocyclyl contains from 1 to 4 heteroatoms, from 1 to 3 heteroatoms, from 1 to 2 heteroatoms, or 1 heteroatom. For example, in various embodiments, a heterocyclyl contains 1 to 4 nitrogen atoms, 1 to 3 nitrogen atoms, 1 to 2 nitrogen atoms, 2 nitrogen atoms and 1 sulfur or oxygen atom, 1 nitrogen atom and 1 sulfur or oxygen atom, or 1 sulfur or oxygen atom. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidinonyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

A "(heterocyclyl)alkyl" is a heterocyclyl group connected, as a substituent, via an alkylene group. Examples include, but are not limited to, imidazolinylmethyl and indolinylethyl.

As used herein, "acyl" refers to —C(=O)R, wherein R is hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. Non-limiting examples include formyl, acetyl, propanoyl, benzoyl, and acryl.

An "O-carboxy" group refers to a "—OC(=O)R" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein.

A "C-carboxy" group refers to a "—C(=O)OR" group in which R is selected from hydrogen, $C_{1-6}$ alkyl, $C_{2-6}$ alkenyl, $C_{2-6}$ alkynyl, $C_{3-7}$ carbocyclyl, aryl, 5-10 membered heteroaryl, and 5-10 membered heterocyclyl, as defined herein. A non-limiting example includes carboxyl (i.e., —C(=O)OH).

A "cyano" group refers to a "—CN" group.
A "cyanato" group refers to an "—OCN" group.
An "isocyanato" group refers to a "—NCO" group.
A "thiocyanato" group refers to a "—SCN" group.
An "isothiocyanato" group refers to an "—NCS" group.
A "sulfinyl" group refers to an "—S(=O)R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

A "sulfonyl" group refers to an "—SO$_2$R" group in which R is selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "S-sulfonamido" group refers to a "—SO$_2$NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-sulfonamido" group refers to a "—N(R$_A$)SO$_2$R$_B$" group in which R$_A$ and R$_b$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, $C_{1-6}$ alkyl, $C_{2-6}$ alkenyl, $C_2$-6 alkynyl, $C_3$-7 carbocyclyl, $C_{6-10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, $C_1$-6 alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "amino" group refers to a "—NR$_A$R$_B$" group in which R$_A$ and R$_B$ are each independently selected from hydrogen, $C_{1-6}$ alkyl, $C_{2-6}$ alkenyl, $C_{2-6}$ alkynyl, $C_{3-7}$ carbocyclyl, $C_{6-10}$ aryl, 5-10 membered heteroaryl, and 5-10 membered heterocyclyl, as defined herein.

An "aminoalkyl" group refers to an amino group connected via an alkylene group.

An "alkoxyalkyl" group refers to an alkoxy group connected via an alkylene group, such as a "$C_{2-8}$ alkoxyalkyl" and the like.

As used herein, a "natural amino acid side chain" refers to the side-chain substituent of a naturally occurring amino acid. Naturally occurring amino acids have a substituent attached to the α-carbon. Naturally occurring amino acids include Arginine, Lysine, Aspartic acid, Glutamic acid, Glutamine, Asparagine, Histidine, Serine, Threonine, Tyrosine, Cysteine, Methionine, Tryptophan, Alanine, Isoleucine, Leucine, Phenylalanine, Valine, Proline, and Glycine.

As used herein, a "non-natural amino acid side chain" refers to the side-chain substituent of a non-naturally occurring amino acid. Non-natural amino acids include β-amino acids ($β^3$ and $β^2$), Homo-amino acids, Proline and Pyruvic acid derivatives, 3-substituted Alanine derivatives, Glycine derivatives, Ring-substituted Phenylalanine and Tyrosine Derivatives, Linear core amino acids and N-methyl amino acids. Exemplary non-natural amino acids are available from Sigma-Aldridge, listed under "unnatural amino acids & derivatives." See also, Travis S. Young and Peter G. Schultz, "Beyond the Canonical 20 Amino Acids: Expanding the Genetic Lexicon," J. Biol. Chem. 2010 285: 11039-11044, which is incorporated by reference in its entirety.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

In some embodiments, substituted group(s) is (are) substituted with one or more substituent(s) individually and independently selected from $C_1$-$C_4$ alkyl, amino, hydroxy, and halogen.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

When two R groups are said to form a ring (e.g., a carbocyclyl, heterocyclyl, aryl, or heteroaryl ring) "together with the atom to which they are attached," it is meant that the collective unit of the atom and the two R groups are the recited ring. The ring is not otherwise limited by the definition of each R group when taken individually. For example, when the following substructure is present:

and $R^1$ and $R^2$ are defined as selected from the group consisting of hydrogen and alkyl, or $R^1$ and $R^2$ together with the nitrogen to which they are attached form a heterocyclyl, it is meant that $R^1$ and $R^2$ can be selected from hydrogen or alkyl, or alternatively, the substructure has structure:

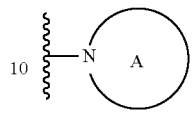

where ring A is a heterocyclyl ring containing the depicted nitrogen.

Similarly, when two "adjacent" R groups are said to form a ring "together with the atoms to which they are attached," it is meant that the collective unit of the atoms, intervening bonds, and the two R groups are the recited ring. For example, when the following substructure is present:

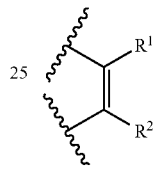

and $R^1$ and $R^2$ are defined as selected from the group consisting of hydrogen and alkyl, or $R^1$ and $R^2$ together with the atoms to which they are attached form an aryl or carbocyclyl, it is meant that $R^1$ and $R^2$ can be selected from hydrogen or alkyl, or alternatively, the substructure has structure:

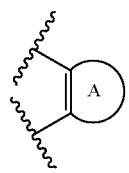

where A is an aryl ring or a carbocyclyl containing the depicted double bond.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

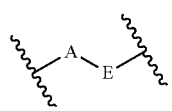

includes the substituent being oriented such that the A is attached at the leftmost attachment point of the molecule as well as the case in which A is attached at the rightmost attachment point of the molecule.

The term "mammal" is used in its usual biological sense. Thus, it specifically includes, but is not limited to, primates, including simians (chimpanzees, apes, monkeys) and humans, cattle, horses, sheep, goats, swine, rabbits, dogs, cats, rats and mice but also includes many other species.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

An "effective amount" or a "therapeutically effective amount" as used herein refers to an amount of a therapeutic agent that is effective to relieve, to some extent, or to reduce the likelihood of onset of, one or more of the symptoms of a disease or condition, and includes curing a disease or condition. "Curing" means that the symptoms of a disease or condition are eliminated; however, certain long-term or permanent effects may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and P. G. M. Green, T. W. Wutts, *Protecting Groups in Organic Synthesis* (3rd ed.) Wiley, New York (1999), which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

In the following schemes, protecting groups for oxygen atoms are selected for their compatibility with the requisite synthetic steps as well as compatibility of the introduction and deprotection steps with the overall synthetic schemes (P. G. M. Green, T. W. Wutts, Protecting Groups in Organic Synthesis (3rd ed.) Wiley, New York (1999)).

If the compounds of the present technology contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

In one embodiment, the methods disclosed herein may include constructing a 39-amino acid peptide backbone using solid-phase peptide synthesis techniques to provide intermediate (II). The peptide backbone includes two $PEG_2$ amide linkers. The method includes an amide coupling reaction between the amine of the terminal $PEG_2$ amide of intermediate (II) and an appropriately substituted carboxylic acid (III) to provide the resin-bound intermediate (IV). In one embodiment, the method involves subjecting intermediate (IV) to hydrolysis under acidic conditions followed by purification to yield the final product (I). (Scheme 1).

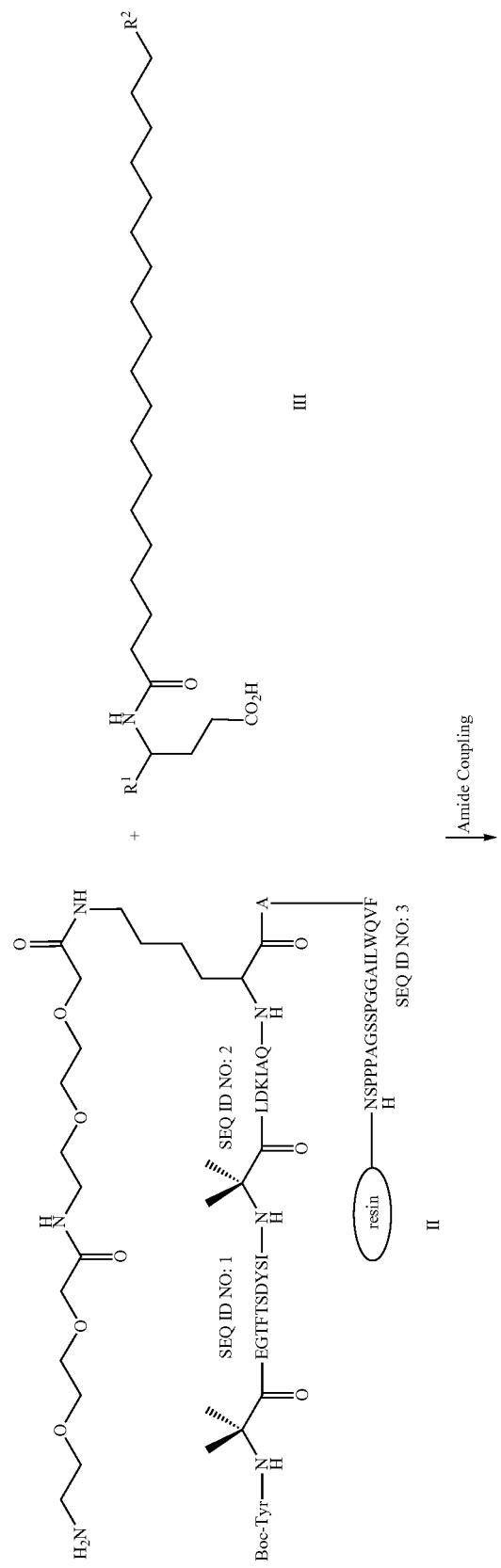

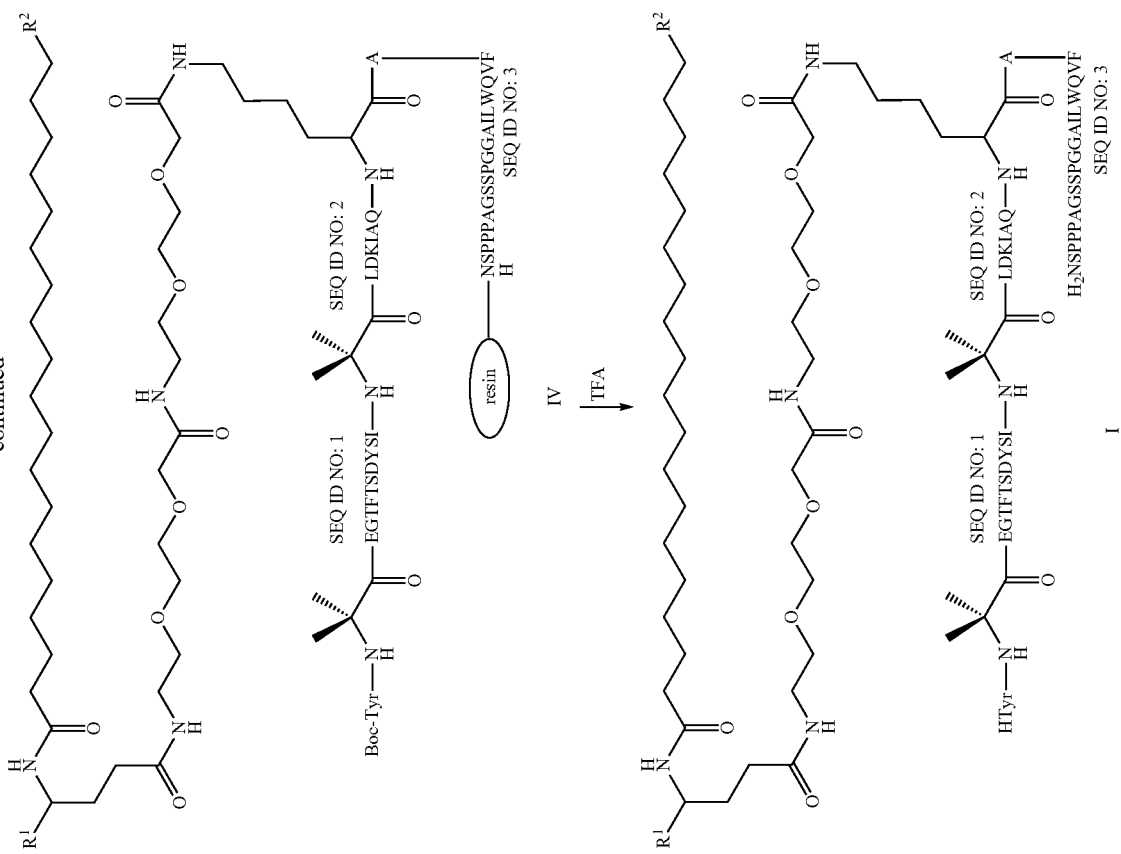

The above example schemes are provided for the guidance of the reader, and collectively represent an example method for making the compounds encompassed herein. Furthermore, other methods for preparing compounds described herein will be readily apparent to the person of ordinary skill in the art in light of the following reaction schemes and examples. Unless otherwise indicated, all variables are as defined above.

Administration and Pharmaceutical Compositions

The compounds are administered at a therapeutically effective dosage. While human dosage levels have yet to be optimized for the compounds described herein, generally, a daily dose may be from about 0.0125 mg/kg to about 120 mg/kg or more of body weight, from about 0.025 mg/kg or less to about 70 mg/kg, from about 0.05 mg/kg to about 50 mg/kg of body weight, or from about 0.075 mg/kg to about 10 mg/kg of body weight. Thus, for administration to a 70 kg person, the dosage range would be from about 0.88 mg per day to about 8000 mg per day, from about 1.8 mg per day or less to about 7000 mg per day or more, from about 3.6 mg per day to about 6000 mg per day, from about 5.3 mg per day to about 5000 mg per day, or from about 11 mg to about 3000 mg per day. The amount of active compound administered will, of course, be dependent on the subject and disease state being treated, the severity of the affliction, the manner and schedule of administration and the judgment of the prescribing physician.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. Oral and parenteral administrations are customary in treating the indications that are the subject of the preferred embodiments.

The compounds useful as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety. Accordingly, some embodiments include pharmaceutical compositions comprising: (a) a safe and therapeutically effective amount of a compound described herein (including enantiomers, diastereoisomers, tautomers, polymorphs, and solvates thereof), or pharmaceutically acceptable salts thereof; and (b) a pharmaceutically acceptable carrier, diluent, excipient or combination thereof.

In addition to the selected compound useful as described above, some embodiments include compositions containing a pharmaceutically-acceptable carrier. The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, subcutaneous, or other parental routes of administration. In some embodiments, the compositions may be in a form suitable for subcutaneous administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropes, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The compositions for intravenous administration may be provided to caregivers in the form of one more solids that are reconstituted with a suitable diluent such as sterile water, saline or dextrose in water shortly prior to administration. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

The compounds and compositions described herein, if desired, may be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compounds and compositions described herein are formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01 99.99 wt % of a compound of the present technology based on the total formulation, with the balance being one or more suitable pharmaceutical excipients. Preferably, the compound is present at a level of about 1 80 wt %. Representative pharmaceutical formulations are described below.

FORMULATION EXAMPLES

The following are representative pharmaceutical formulations containing a compound of formula I.

Formulation Example 1—Tablet Formulation

The following ingredients are mixed intimately and pressed into single scored tablets.

| Ingredient | Quantity per tablet, mg |
|---|---|
| Compounds disclosed herein | 400 |
| cornstarch | 50 |
| croscarmellose sodium | 25 |
| lactose | 120 |
| magnesium stearate | 5 |

Formulation Example 2—Capsule Formulation

The following ingredients are mixed intimately and loaded into a hard-shell gelatin capsule.

| Ingredient | Quantity per capsule, mg |
|---|---|
| Compounds disclosed herein | 200 |
| lactose, spray-dried | 148 |
| magnesium stearate | 2 |

Formulation Example 3—Suspension Formulation

The following ingredients are mixed to form a suspension for oral administration.

| Ingredient | Amount |
|---|---|
| Compounds disclosed herein | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4—Injectable Formulation

The following ingredients are mixed to form an injectable formulation.

| Ingredient | Amount |
|---|---|
| Compounds disclosed herein | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Amount |
|---|---|
| Compounds disclosed herein | 500 mg |
| Witepsol ® H-15 | balance |

Methods of Treatment

The compounds disclosed herein or their tautomers and/or pharmaceutically acceptable salts thereof can effectively act as GIP/GLP1 dual receptor agonists. Some embodiments provide pharmaceutical compositions comprising one or more compounds disclosed herein and a pharmaceutically acceptable excipient.

Some embodiments provide a method of preventing, treating, or ameliorating one or more fatty liver diseases in a subject. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

Some embodiments provide a method preventing, treating, or ameliorating steatosis, non-alcoholic steatohepatitis and non-alcoholic fatty liver disease. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

In some embodiments, the method of administering one or more of the compounds disclosed herein results in the prevention, treatment, or amelioration, of a fibrosis, fibrotic condition, or fibrotic symptoms. In some embodiments, the method includes administering a pharmaceutically acceptable salt thereof of one or more of the compounds disclosed herein.

In some embodiments, the compounds and compositions comprising the compounds described herein can be used to treat a host of conditions arising from fibrosis or inflammation, and specifically including those associated with myofibroblast differentiation. Example conditions include progressive liver fibrosis (alcoholic, viral, autoimmune, metabolic and hereditary chronic disease), renal fibrosis (e.g., resulting from chronic inflammation, infections or type II diabetes), lung fibrosis (idiopathic or resulting from environmental insults including toxic particles, sarcoidosis, asbestosis, hypersensitivity pneumonitis, bacterial infections including tuberculosis, medicines, etc.), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia, other blood disorders), cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, diabetic nephropathy, non-alcoholic steatohepatitis, primary sclerosing cholangitis, corneal fibrosis, liver cirrhosis, fibrotic complications of surgery, chronic allograft vasculopathy and/or chronic rejection in transplanted organs, ischemic reperfusion injury associated fibrosis, injection fibrosis, cirrhosis, diffuse parenchymal lung disease, post-vasectomy pain syndrome, and rheumatoid arthritis diseases or disorders.

In some embodiments, the method of administering one or more of the compounds disclosed herein results in the reduction in the amount of extracellular matrix proteins present in one or more tissues of said subject. In some embodiments, the method includes administering a pharmaceutically acceptable salt thereof of one or more of the compounds disclosed herein.

In some embodiments, the method of administering one or more of the compounds disclosed herein results in the reduction in the amount of collagen present in one or more tissues of said subject. In some embodiments, the method includes administering a pharmaceutically acceptable salt thereof of one or more of the compounds disclosed herein.

In some embodiments, the method of administering one or more of the compounds disclosed herein results in the reduction in the amount of Type I, Type Ia, or Type III collagen present in one or more tissues of said subject. In some embodiments, the method includes administering a pharmaceutically acceptable salt thereof of one or more of the compounds disclosed herein.

Some embodiments provide a method of preventing, treating, or ameliorating one or more of liver fibrosis, renal fibrosis, biliary fibrosis, pancreatic fibrosis, nonalcoholic steatohepatitis, non-alcoholic fatty liver disease, chronic kidney disease, diabetic kidney disease, primary sclerosing cholangitis, primary biliary cirrhosis, or idiopathic fibrosis in a subject. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

Some embodiments provide a method of preventing, treating, or ameliorating one or more of nonalcoholic steatohepatitis, non-alcoholic fatty liver disease, chronic kidney disease, diabetic kidney disease, primary sclerosing cholangitis, or primary biliary cirrhosis in a subject. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

Some embodiments provide a method of preventing, treating, or ameliorating one or more metabolic disorders or metabolic syndromes. In some embodiments, said disease or disorder is atherosclerosis, diabetes, hyperglycemic diabetes, type 2 diabetes mellitus, dyslipidemia, hypercholesterolemia, hyperlipidemia, hypertension, hypoglycemia, obesity, or prader-willi syndrome. In some embodiments, the method includes administering one or more of the compounds disclosed herein to a subject in need thereof. In some embodiments, the method includes administering a pharmaceutically acceptable salt thereof of one or more of the compounds disclosed herein to a subject in need thereof.

In some embodiments, the method of administering one or more of the compounds disclosed herein results in the compound activating a glucose-dependent insulinotropic polypeptide (GIP) receptor. In some embodiments, the method of administering one or more of the compounds disclosed herein results in the compound activating a glucagon-like peptide-1 (GLP-1) receptor. In some embodiments, the method of administering one or more of the compounds disclosed herein results in the compound activating the GIP receptor and the GLP-1 receptor.

Some embodiments include co-administering a compound, composition, and/or pharmaceutical composition described herein, with an additional medicament. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. In another embodiment, the agents are administered sequentially. In one embodiment the agents are administered through the same route, such as orally. In another embodiment, the agents are administered through different routes, such as one being administered subcutaneously, another being administered orally and another being administered i.v.

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples. The following examples will further describe the present invention, and are used for the purposes of illustration only, and should not be considered as limiting.

EXAMPLES

General Procedures

It will be apparent to the skilled artisan that methods for preparing precursors and functionality related to the compounds claimed herein are generally described in the literature. In these reactions, it is also possible to make use of variants which are themselves known to those of ordinary skill in this art, but are not mentioned in greater detail. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as March Advanced Organic Chemistry (Wiley), Carey and Sundberg, Advanced Organic Chemistry (incorporated herein by reference in their entirety) and the like. All the intermediate compounds of the present invention were used without further purification unless otherwise specified.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts Protecting Groups in Organic Synthesis, 4th Ed., John Wiley & Sons (2007), incorporated herein by reference in its entirety.

The following example schemes are provided for the guidance of the reader, and represent preferred methods for making the compounds exemplified herein. These methods are not limiting, and it will be apparent that other routes may be employed to prepare these compounds. Such methods specifically include solid phase based chemistries, including combinatorial chemistry. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

The following abbreviations have the indicated meanings:
Aib=aminoisobutyric acid
Bn=benzyl
Boc=tert-butoxycarbonyl
Bu=butyl
DMF=dimethylformamide
EDC=1-ethyl-3-(3-dimethylaminopropyl)carbodiimide
Et=ethyl
HATU=hexafluorophosphate azabenzotriazole tetramethyl uranium
HBTU=hexafluorophosphate benzotriazole tetramethyl uranium
HMDS=hexamethyldisilazane
HPLC=high-performance liquid chromatography
Me=methyl
NaHMDS=sodium hexamethyldisilazide
NMR=nuclear magnetic resonance
PCC=pyridinium chlorochromate
PEG=polyethylene glycol
Ph=phenyl
tBu=tert-butyl
TFA=trifluoroacetic acid
THF=tetrahydrofuran
TMS=trimethylsilyl The following example schemes are provided for the guidance of the reader, and collectively represent an example method for making the compounds provided herein. Furthermore, other methods for preparing compounds described herein will be readily apparent to the person of ordinary skill in the art in light of the following reaction schemes and examples. Unless otherwise indicated, all variables are as defined above.

Example 1

Synthesis of Intermediate 1 (INT 1)

Methyl 7-bromoheptanoate is treated with triphenylphosphine to form the corresponding phosphonium salt. The salt is treated with one equivalent of NaHMDS to make an ylide, which is reacted immediately in a Wittig reaction with the aldehyde from PCC oxidation of 12-bromo-1-dodecanol. The resulting bromo alkene is hydrogenated, and treated with dibenzyl phosphite in weak base to form a phosphonate ester. Hydrolysis of the methyl carboxylate provides desired INT 1 having a terminal carboxylic acid and a dibenzyl phosphonate.

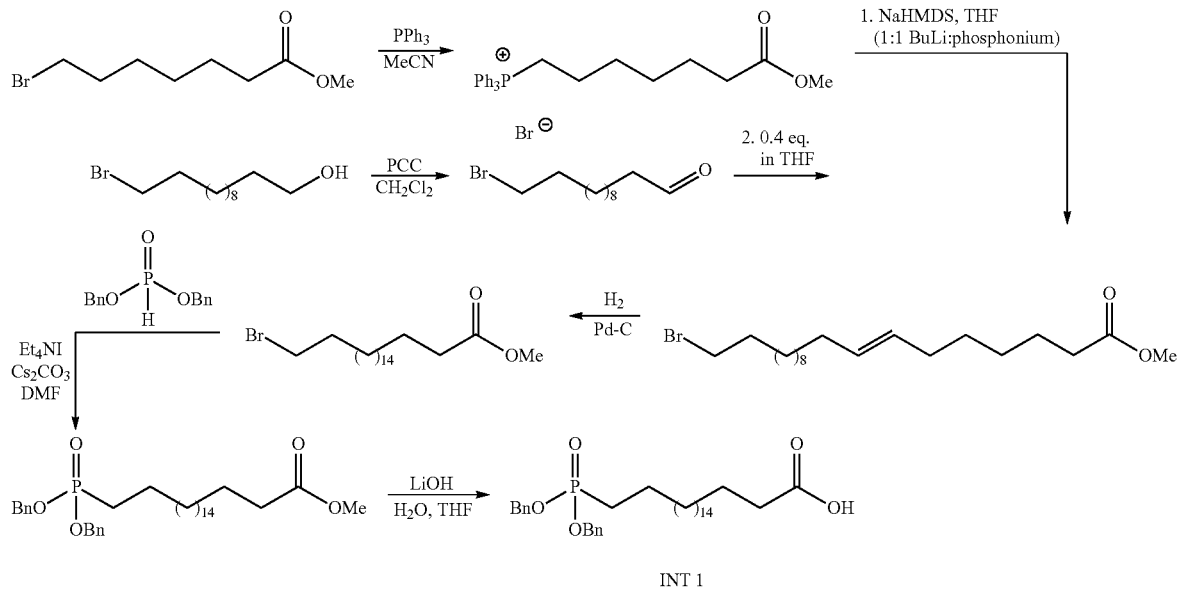

Synthesis of Intermediate 2 (INT 2)

Docosanedioic acid is coupled to benzyl alcohol with EDC·HCl and DMAP in THF to give INT 2 as the mono-benzyl ester.

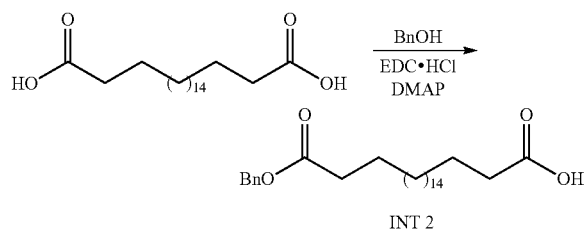

Synthesis of Intermediate 3 (INT 3)

t-Butyl 4-hydroxybutanoate undergoes a Swern oxidation to give an aldehyde. The aldehyde is condensed with (R)-1-amino-2-methoxy-1-phenylethane to form an imine. Addition of the lithium salt of diethyl phosphite in THF generates an α-aminophosphonate, which undergoes hydrogenolysis to cleave the N-alkyl group and provide INT 3 with a free primary amine, a t-butyl ester, and a diethyl phosphonate ester. The optical purity of INT 3 was confirmed to be at least 96% by 1H NMR through Mosher's amide analysis.

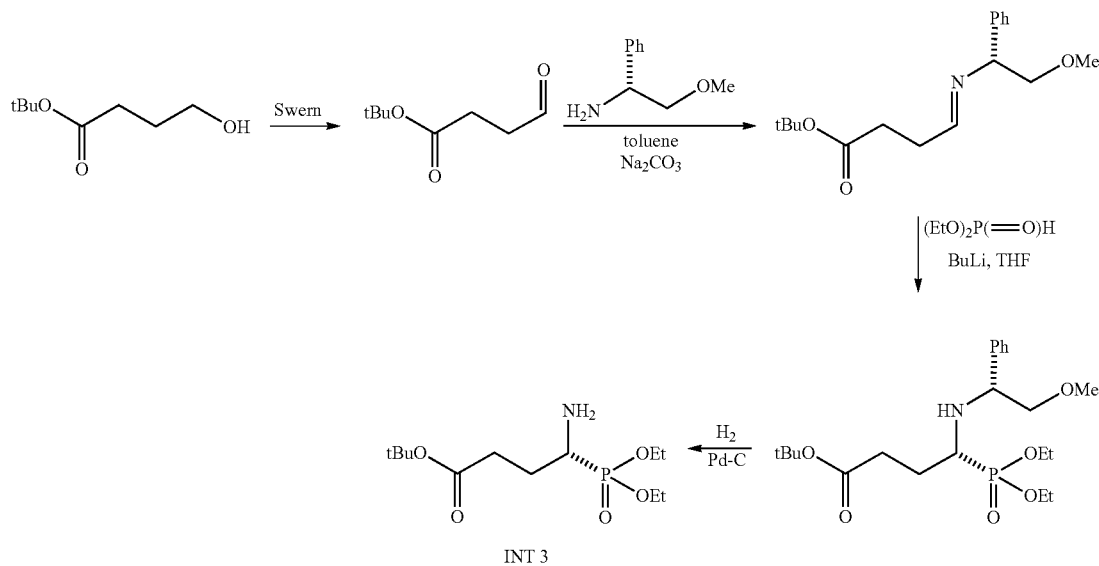

Synthesis of Intermediate 4 (INT 4)

INT 1 is coupled with the 1-t-butyl ester of D-glutamic acid in the presence of HATU and triethylamine in DMF to provide INT 4.

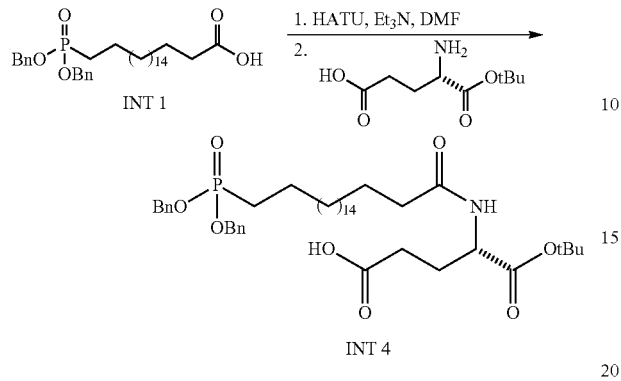

Synthesis of Intermediate 5 (INT 5)

INT 2 is coupled with INT 3 in the presence of HATU and triethylamine in DMF to prepare a new amide linkage. Cleavage of the ethyl phosphonate esters with TMS-Br gives the free phosphonic acid. Re-esterification with a large excess of the benzyl ester of N,N'-diisopropylcarbamimidic acid provides the corresponding dibenzyl phosphonate. The t-butyl ester is cleaved with TFA to provide INT 5.

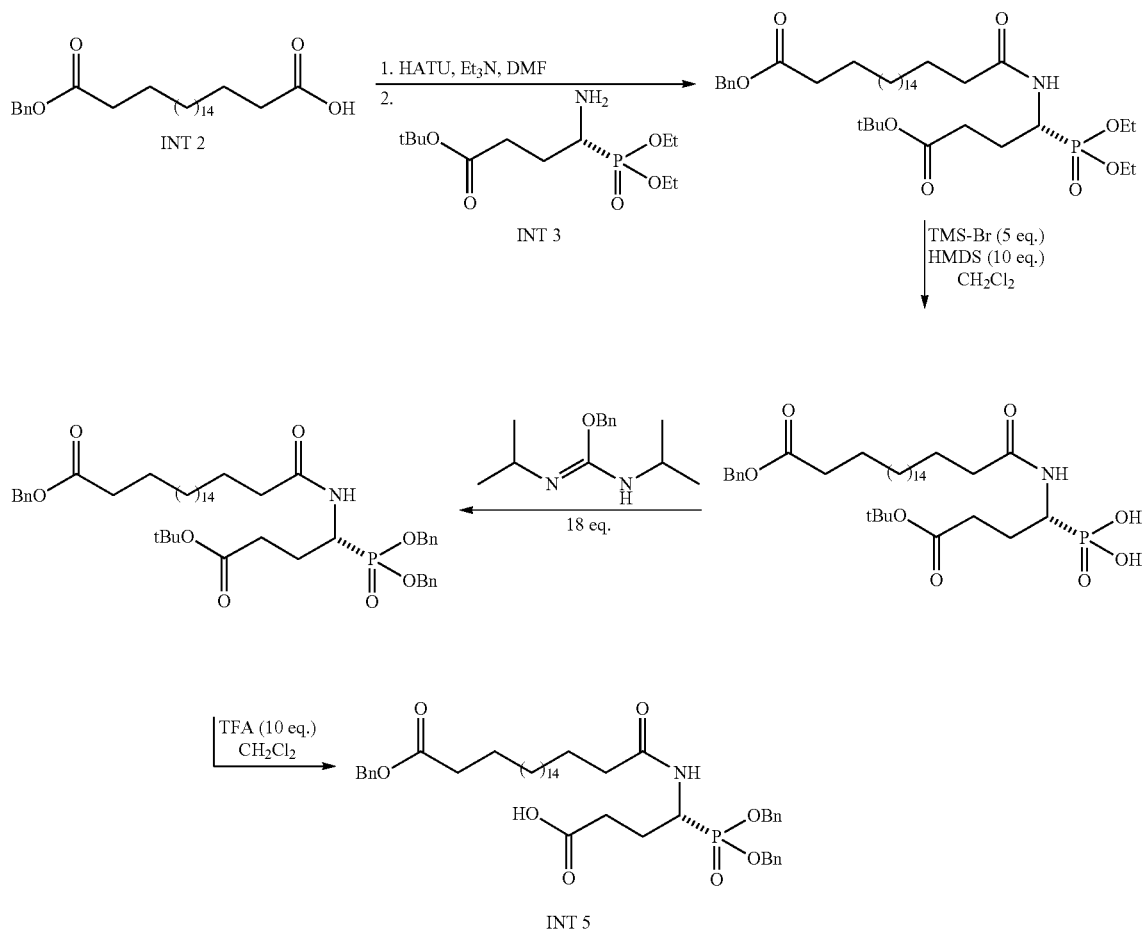

Synthesis of Intermediate 6 (INT 6)

INT 1 is coupled with INT 3 in the presence of HATU and triethylamine in DMF to provide a new amide linkage. Cleavage of the benzyl and ethyl phosphonate esters with TMS-Br gives both free phosphonic acids. Re-esterification with a large excess of the benzyl ester of N,N'-diisopropylcarbamimidic acid provides the corresponding tetrabenzyl diphosphonate ester. The t-butyl ester is cleaved with TFA to give INT 6.

Example 2

Synthesis of Common Peptide Backbone

The 39-amino acid peptide backbone is constructed using solid-phase peptide synthesis techniques with diimide, HATU, or HBTU activation for amide linkage synthesis on a Rink resin. Reagent selection varies based on the identity of the amino acids being connected. The R-group of lysine-19 was extended with two PEG$_2$ amide linkers. The entire backbone is synthesized on the resin before coupling INT 4, INT 5, or INT 6 to the amino terminus of the lysine-bound linker.

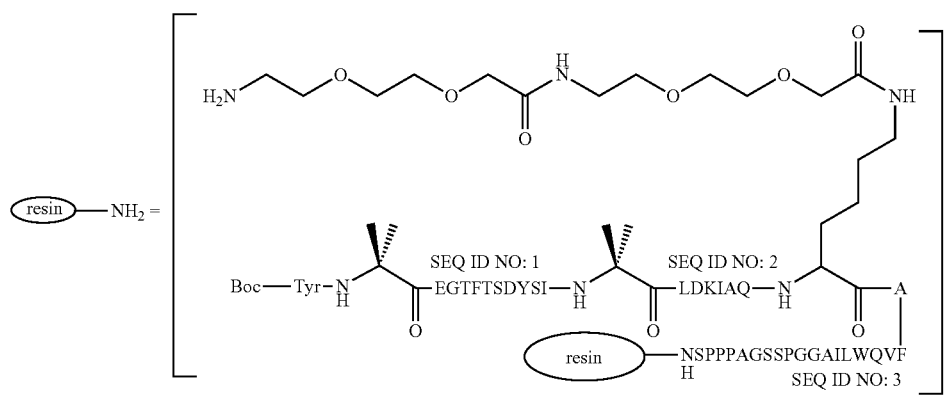

Example 3
Synthesis of Compound 4
The peptide backbone is coupled to INT 4 to give resin-bound, protected Compound 4. Cleavage of the resin, protecting groups on the peptide chain, and benzyl esters of INT 4 with TFA provides Compound 4, which is purified through HPLC.
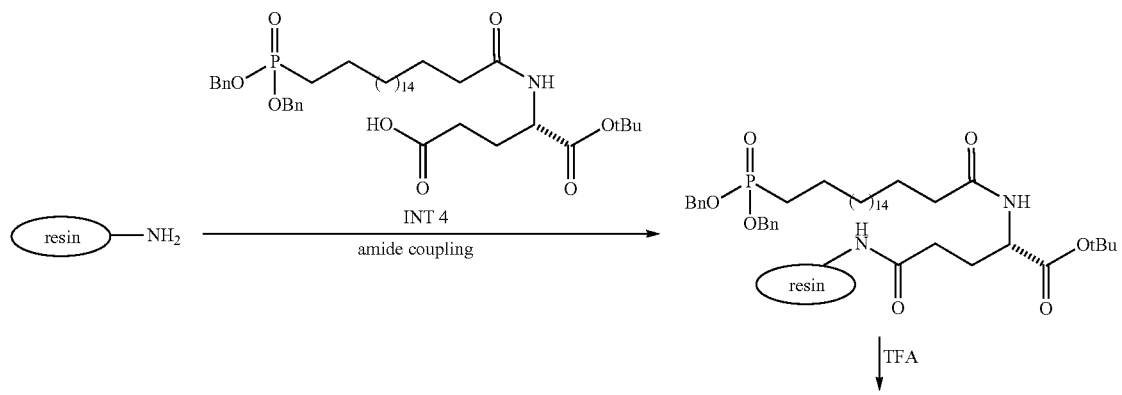
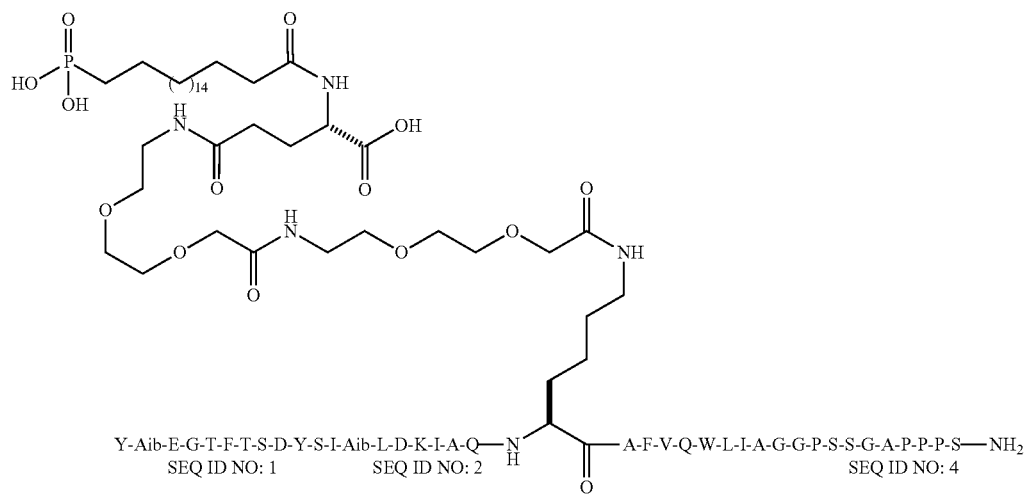

Example 4
Synthesis of Compound 8
The peptide backbone is coupled to INT 5 to give resin-bound, protected Compound 8. Cleavage of the resin, protecting groups on the peptide chain, and benzyl esters of INT 4 with TFA provides Compound 8, which is purified through HPLC.
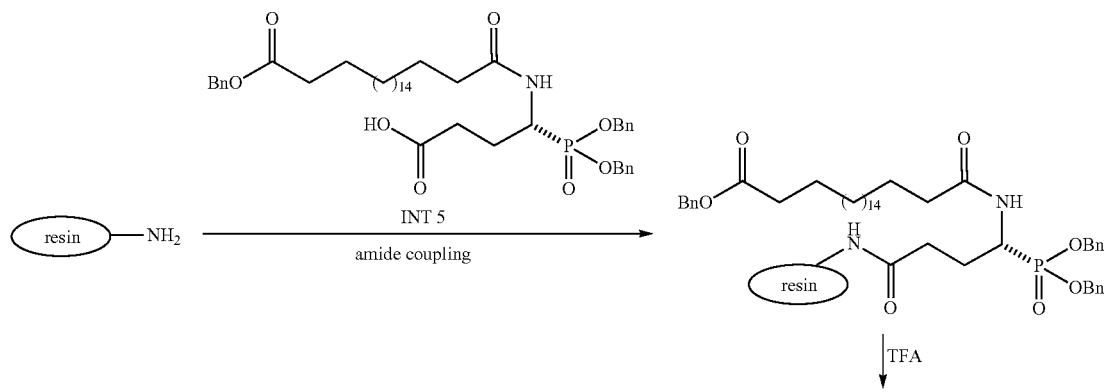
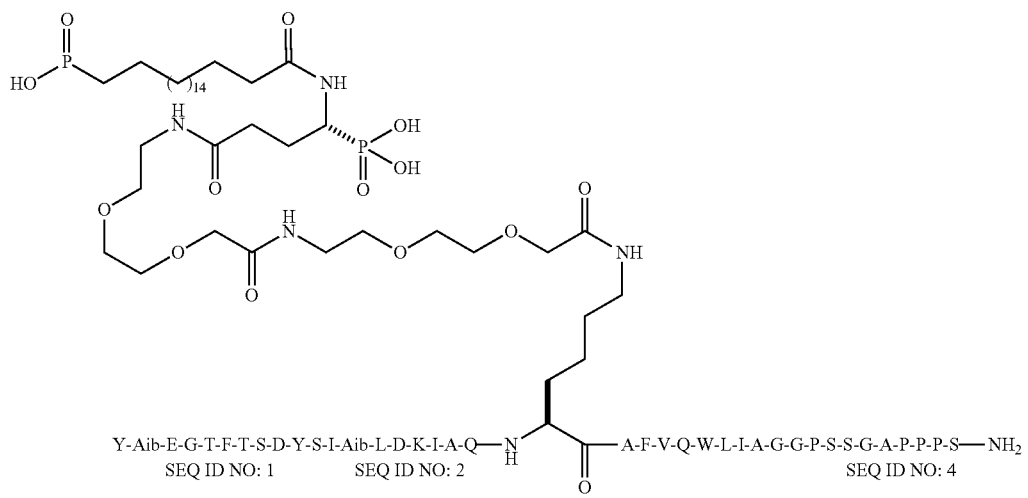

Example 5

Synthesis of Compound 12

The peptide backbone is coupled to INT 6 to give resin-bound, protected Compound 12. Cleavage of the resin, protecting groups on the peptide chain, and benzyl esters of INT 4 with TFA provides Compound 12, which is purified through HPLC.

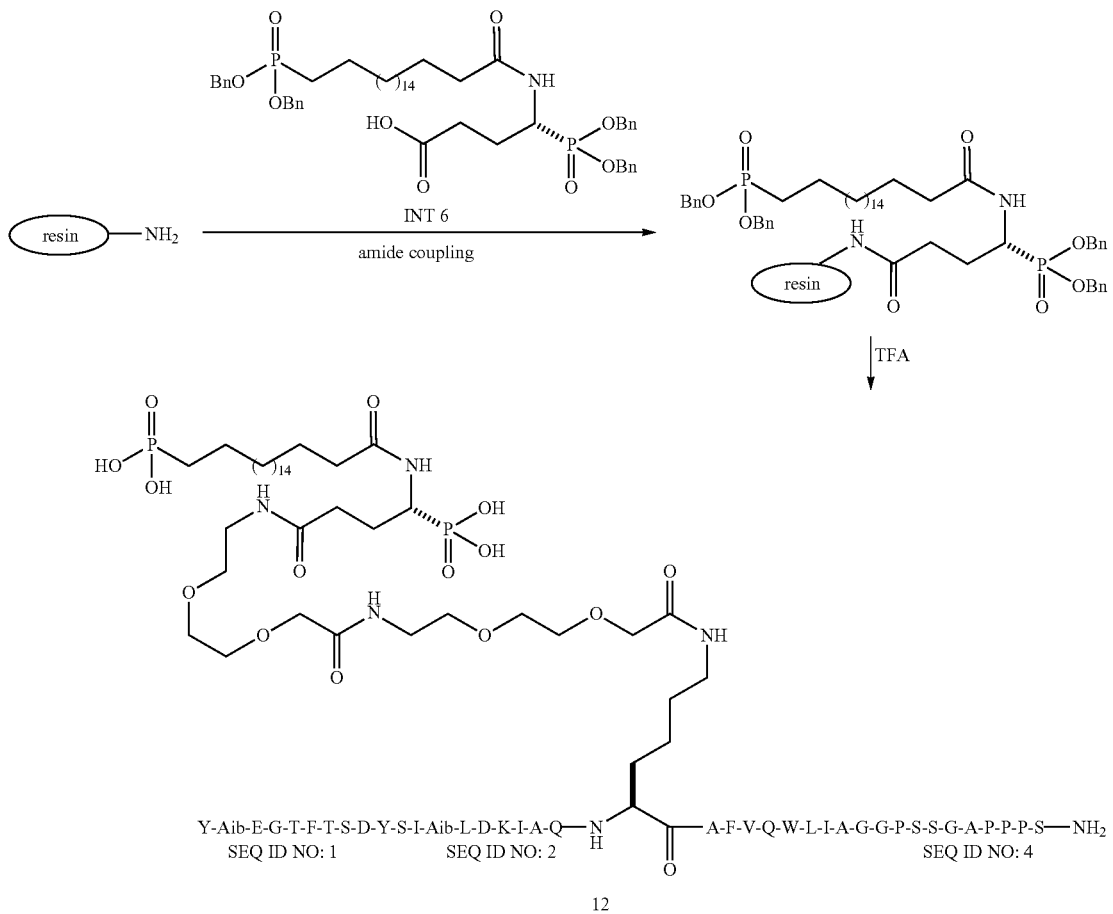

12

Example 6

In-Vitro GLP-1 and GIP Binding Activity

Binding data for tirzepatide, Compound 4, Compound 8 and Compound 12, for two human recombinant G protein coupled receptors, GLP-1 and GIP, was obtained using TagLite® binding assay and Epics Therapeutics cell lines. Agonist activity of the test compounds is expressed as a percentage of the activity of the reference agonist at its $IC_{100}$ concentration, as shown in Table 1.

TABLE 1

| | GLP-1 receptor | | GIP receptor | |
|---|---|---|---|---|
| Compound ID | % Binding avg at $C_{Max}$ | IC 50 (nM) | % Binding avg at $C_{Max}$ | IC 50 (nM) |
| Tirzepatide | 0.20 | 281 | −1.21 | 188 |
| 4 | −0.11 | 105 | −1.34 | 153 |
| 8 | 0.32 | 288 | −1.20 | 223 |
| 12 | 0.09 | 129 | −1.47 | 137 |

Example 7

Biological Effects of Compounds in Mice

NASH was induced in mice by feeding mice a Gubra amylin NASH (GAN) diet as described in Boland et al. *World J Gastroenterol.* 2019, 25(33): 4904-4920. One week prior to administration of a first dose of compounds, the mice were weighed and randomized, and their food intake was measured. Mice were randomly assigned to dosing groups, with twelve mice per group. Assigned dosage groups were: tirzepatide (10 mg/kg); Compound 4 (10 mg/kg); Compound 8 (10 mg/kg); Compound 12 (10 mg/kg); One group was mock treated with vehicle only as a control. Compound dose titration (nmol/kg): 0.6 (day 0), 1.2 (day 1), 2.4 (day 2), 4.8 (day 3), 4.8 (day 4), 12 (day 5), 30.0 (from day 6).

After two weeks, animals were sacrificed. Plasma enzymes (P-ALT (alanine aminotransferase) and P-AST (aspartate aminotransferase)), total plasma triglycerides, and total plasma cholesterol were measured, and terminal necropsy of each liver was carried out, determining relative liver weight as a percentage of body weight, assaying total liver biochemistry including total liver triglycerides, plasma insulin and total liver cholesterol, as well as histological evaluation of Galectin-3, and alpha-smooth muscle actin.

Liver triglyceride (TG) levels are shown in Table 2. The data shows that administration of Compound 4, Compound 8 or Compound 12 resulted in lower relative and total liver triglycerides as compared to administration of tirzepatide or vehicle alone. Liver Galectin-3 (Gal-3) levels as determined by histological quantitative assessment are shown in Table 2.

The data shows that administration of Compound 4, Compound 8 or Compound 12 resulted in lower relative and total liver Galectin-3 as compared to administration of tirzepatide or vehicle alone. Alpha-smooth muscle actin (α-SMA) levels as determined by histological quantitative assessment are shown in Table 2. The data shows that administration of Compound 4, Compound 8 or Compound 12 resulted in lower relative and total liver alpha-smooth muscle actin as compared to administration of tirzepatide.

TABLE 2

| Compound ID | TG Relative (mg per/ g liver) | TG Total (mg per/ liver) | Gal-3 Relative (percent fractional area) | Gal-3 Total (mg) | α-SMA Relative (percent fractional area) | α-SMA Total (mg) |
| --- | --- | --- | --- | --- | --- | --- |
| Vehicle | 63 ± 5 | 195 ± 13 | 5.1 ± 0.3 | 172 ± 22 | 3.2 ± 0.5 | 104 ± 22 |
| Tirzepatide | 42 ± 6 | 80 ± 11 | 6.7 ± 0.5 | 138 ± 17 | 5.3 ± 0.8 | 108 ± 22 |
| 4 | 37 ± 3 | 70 ± 5 | 6.3 ± 0.3 | 137 ± 15 | 4.8 ± 0.6 | 102 ± 10 |
| 8 | 40 ± 3 | 75 ± 7 | 5.8 ± 0.6 | 117 ± 12 | 4.3 ± 0.5 | 83 ± 8 |
| 12 | 35 ± 3 | 63 ± 5 | 5.7 ± 0.5 | 113 ± 10 | 4.4 ± 0.6 | 84 ± 8 |

TG: Triglycerides;
Gal-3: Galectin-3;
α-SMA: α-smooth muscle actin

Example 8

HSA Modulated In-Vitro GLP-1 and GIP Binding Activity

The binding assay of Example 6 was repeated for the compounds tirzepatide (TRZ), Compound 4 and Compound 12 with assays performed in the presence or absence of 2% human serum albumin (HSA). The ratio of compound-receptor binding with 2% HSA to compound-receptor binding with 0% HSA is listed in Table 3. Tirzepatide has an HSA ratio of 12.8 and 5.82 for the GLP-1 receptor and GIP receptor, respectively. Compound 4 has an HSA ratio of 6.42 and 1.25 for the GLP-1 receptor and GIP receptor, respectively. Compound 12 has an HSA ratio of 5.26 and 1.70 for the GLP-1 receptor and GIP receptor, respectively. The larger HSA ratios of tirzepatide when compared to Compound 4 and Compound 12 indicates that the binding affinity of tirzepatide for albumin is greater than that of Compound 4 or of Compound 12.

Mean half life values are shown in Table 4. The data shows that administration of Compound 4 or Compound 12 resulted in significantly greater persistence in the blood stream as compared to administration of tirzepatide. The mean half life of Compound 4 is almost twice an long as compared to tirzepatide.

TABLE 4

| Compound ID | Half Life (h) |
| --- | --- |
| Tirzepatide | 63.2 |
| 4 | 118 |
| 12 | 104 |

In previous studies, a direct correlation between albumin binding affinity and in vivo half life was observed; compounds having a longer half life displayed greater albumin binding affinity. (Lau, J., et al. J. Med. Chem. 2015, 58, 7370-7380). As described above, the experiment of Example 8 indicated that the binding affinity of tirzepatide for albumin is greater than that of Compound 4 or of Compound 12. In contrast, the pharmacokinetic experiments described in this example determined the half life of tirzepatide, Compound 4 and Compound 12 to be 63.2 h, 118 h and 104 h, respectively. The longer half life of Compound 4 and Compound 12 when compared to that of tirzepatide is an unexpected result in view of the previous studies. The smaller HSA ratios of Compound 4 and Compound 12 indicate that Compound 4 and Compound 12 would be expected to have lower albumin binding affinity and shorter half life relative to tirzepatide. The longer half life for Compound 4 or Compound 12 relative to tirzepatide is opposite of the expected results.

Example 10

Pharmacokinetics Studies of Formulations

The SC dosing experiments described in Example 9 were repeated with different formulations of tirzepatide and Compound 4. Formulation 1 included the compound in a vehicle of 0.1% bovine serum albumin in phosphate buffered saline solution. Formulation 2 included the compound in 40%

TABLE 3

| | GLP-1 receptor | | | | | GIP receptor | | | | |
| --- | --- | --- | --- | --- | --- | --- | --- | --- | --- | --- |
| | % Binding avg at $C_{Max}$ | | IC 50 (nM) | | Ratio of | % Binding avg at $C_{Max}$ | | IC 50 (nM) | | Ratio of |
| Sample ID | 2% HSA | 0% HSA | 2% HSA | 0% HSA | HSA/ No HSA | 2% HSA | 0% HSA | 2% HSA | 0% HSA | HSA/ No HSA |
| TRZ | 33.01 | −0.14 | 3409 | 266 | 12.8 | 10.07 | −3.05 | 1840 | 316 | 5.82 |
| 4 | 13.12 | 0.03 | 988 | 154 | 6.42 | 6.68 | −4.57 | 331 | 264 | 1.25 |
| 12 | 12.04 | 0.22 | 763 | 145 | 5.26 | 5.52 | −3.33 | 436 | 256 | 1.70 |

Example 9

Pharmacokinetics of Compounds in Monkeys

Subcutaneous (SC) dosing of the compounds in a vehicle of 0.1% bovine serum albumin in phosphate buffered saline solution was performed with male cynomolgus monkeys. Assigned dosage groups were: tirzepatide (0.2 mg/kg); Compound 4 (0.2 mg/kg); Compound 12 (0.2 mg/kg). Samples were obtained at 1, 4, 8, 12, 24, 48, 72, 96, 120, 168, 192, 240 and 336 hours after the single dose was administered.

propylene glycol and 60% 10 mM pH 6 citrate buffer solution. Assigned dosage groups were administered tirzepatide (0.2 mg/kg) or Compound 4 (0.2 mg/kg) over 21 days.

Mean half life values for the two formulations are shown in Table 5. The data shows that administration of Compound 4 in Formulation 1 and Formulation 2 resulted in significantly greater persistence in the blood stream as compared to administration of tirzepatide in the identical formulation. The mean half life of Compound 4 in Formulation 1 is almost twice an long as compared to tirzepatide. Formulation 2 resulted in a mean half life of Compound 4 that is twice as long when compared to tirzepatide.

TABLE 5

|  | Compound ID | Half Life (h) |
|---|---|---|
| Formulation 1 | Tirzepatide | 66.2 |
|  | 4 | 106 |
| Formulation 2 | Tirzepatide | 59.8 |
|  | 4 | 120 |

The unexpected results described in Example 9 were also observed in this example when the compounds were administered in Formulation 1 and Formulation 2. The longer half life in Formulation 1 and Formulation 2 for Compound 4 relative to tirzepatide is opposite of the expected results in view of the HSA studies described above.

Example 11

Solubility of Compounds

A 50 mM phosphate buffer was prepared according to U.S. Pharmacopoeia (USP) guidelines. A mass of 27.22 g potassium phosphate monobasic was diluted with water to prepare 1000 mL of solution. A volume of 250 mL of the monobasic potassium phosphate solution and a volume of 22.4 mL of 1 M NaOH solution was diluted with water to 1000 mL. The pH of the resultant buffer solution was measured as 6.83. Solubility studies were performed at ambient conditions and were designed to prepare a solution with maximum concentration of approximately 20 mg/mL. An initial volume of 100 µL of buffer was added to approximately 1-4 mg sample of tirzepatide (TRZ), Compound 4, Compound 8, and Compound 12 followed by swirling or vortex mixing. Additional buffer was added in increments of less than 1 mL to up to a maximum of about 200 mL. Quantitative solubility (QNT) was reported in mg/mL. Qualitative solubility (QLT) based on visual observations was described using USP protocol. The results are listed in Table 6.

TABLE 6

| Compound ID | Sample Mass (mg) | Buffer Volume (mL) | QNT (mg/mL) | Observations | QLT |
|---|---|---|---|---|---|
| TRZ | 1.71 | 0.7 | >2 | The sample began to dissolve in 100 µL with particles visible. Hair like fibers were visible when fully dissolved. | Slightly Soluble |
| 4 | 1.56 | 0.8 | >2 | Compound completely dissolved. | Slightly Soluble |
| 8 | 1.02 | 7 | >0.2 | The sample began to dissolve in 0.5 mL with particles visible. Particles were visible when fully dissolved. | Very Slightly Soluble |
| 12 | 1.13 | 0.2 | >5 | Compound completely dissolved. | Slightly Soluble |

Unlike TRZ, Compounds 4 and 12 were observed to completely dissolve and Compound 12 had quantitatively higher solubility than TRZ.

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Although the invention has been described with reference to embodiments and examples, it should be understood that numerous and various modifications can be made without departing from the spirit of the invention. Accordingly, the invention is limited only by the following claims.

What is claimed is:

1. A pharmaceutical composition comprising a pharmaceutically acceptable excipient and a compound, or a pharmaceutically acceptable salt thereof, to a subject in need thereof, wherein the compound has the structure of formula I:

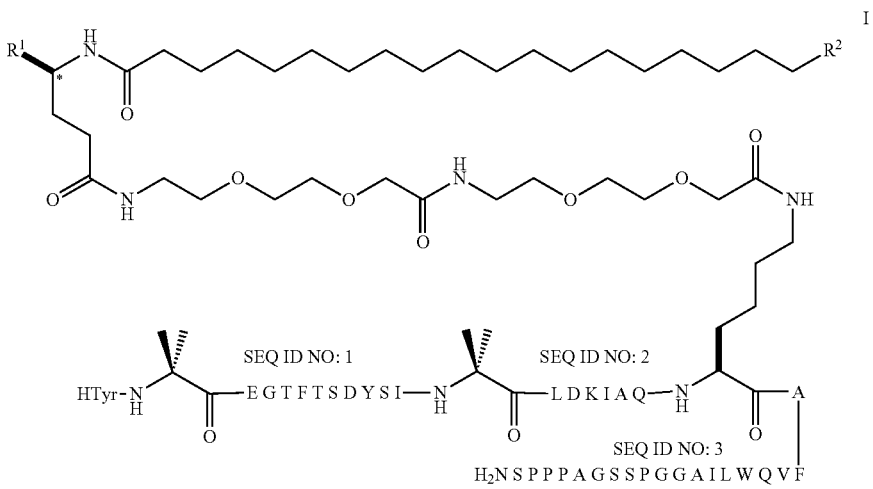

wherein:
"*" indicates a chiral carbon with "S" configuration or "R" configuration;
$R^1$ is selected from the group consisting of —C(=O)(OZ$^1$), —P(=O)(X)(Y) and a 5-10 membered heteroaryl containing 1-2 heteroatoms selected from N, O and S optionally substituted with 1-2 $R^7$ independently selected from halogen, $C_{1-6}$ alkyl, haloC$_{1-6}$ alkyl, haloC$_{1-6}$ alkoxy, —OR$^5$, $C_{3-10}$ cycloalkyl, $C_{6-10}$ aryl, 5-10 membered heteroaryl and 5-10 membered heterocyclyl;

$R^2$ is selected from the group consisting of —C(=O)(OZ$^2$), —P(=O)(X)(Y) and a 5-10 membered heteroaryl containing 1-2 heteroatoms selected from N, O and S optionally substituted with 1-2 $R^7$ independently selected from halogen, $C_{1-6}$ alkyl, haloC$_{1-6}$ alkyl, haloC$_{1-6}$ alkoxy, —OR$^5$, $C_{3-10}$ cycloalkyl, $C_{6-10}$ aryl, 5-10 membered heteroaryl and 5-10 membered heterocyclyl;
each $R^7$ is independently selected from the group consisting of halogen, $C_{1-6}$ alkyl, haloC$_{1-6}$ alkyl, haloC$_{1-6}$ alkoxy, $C_{1-6}$ alkoxy, $C_{3-10}$ cycloalkyl, $C_{6-10}$ aryl, 5-10 membered heteroaryl and 5-10 membered heterocyclyl;
X and Y each are independently selected from the group consisting of —OR$^4$, NR$^5$R$^6$, $C_{1-6}$ alkyl and haloC$_{1-6}$ alkyl;
each $R^4$ is independently selected from the group consisting of hydrogen, $C_{1-6}$ alkyl, haloC$_{1-6}$ alkyl, $C_{6-10}$ aryl and $C_{6-10}$ aryl alkyl;
each $R^5$ is independently hydrogen or $C_{1-6}$ alkyl;
each $R^6$ is independently hydrogen or $C_{1-6}$ alkyl; and
$Z^1$ and $Z^2$ each are independently selected from the group consisting of hydrogen, $C_{1-6}$ alkyl, haloC$_{1-6}$ alkyl, $C_{3-10}$ cycloalkyl, $C_{6-10}$ aryl and ($C_{6-10}$ aryl) $C_{1-6}$ alkyl, wherein at least one of $Z^1$ and $Z^2$ is not hydrogen.

2. The pharmaceutical composition of claim 1, wherein:
$Z^1$ and $Z^2$ each are independently selected from the group consisting of hydrogen, $C_{1-6}$ alkyl, haloC$_{1-6}$ alkyl, $C_{3-10}$ cycloalkyl, and $C_{6-10}$ aryl;
X and Y each are independently selected from the group consisting of —OR$^4$, NR$^5$R$^6$, $C_{1-6}$ alkyl and haloC$_{1-6}$ alkyl;
each $R^4$ is independently selected from the group consisting of hydrogen, $C_{1-6}$ alkyl, and haloC$_{1-6}$ alkyl.

3. The pharmaceutical composition of claim 1, wherein the compound has the structure of formula I-a:

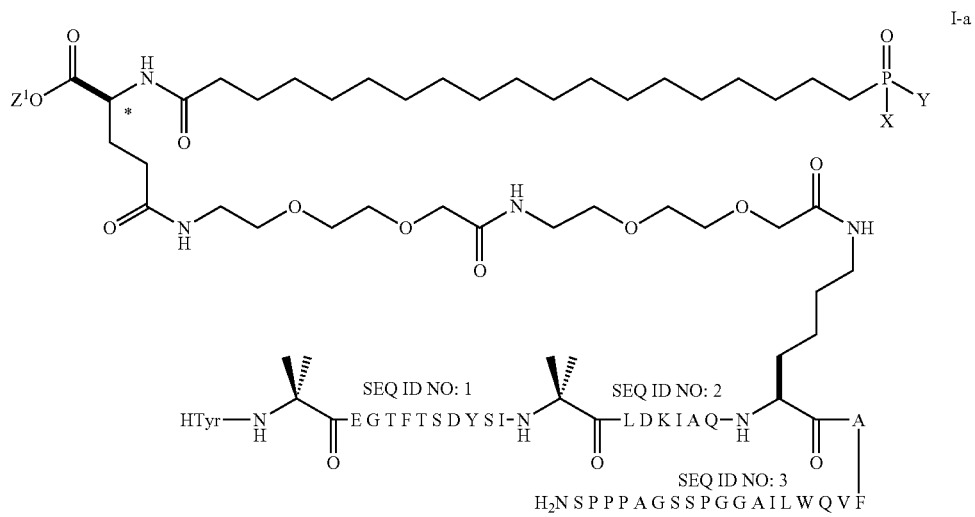

or a pharmaceutically acceptable salt thereof.

4. The pharmaceutical composition of claim 3, wherein $Z^1$ is selected from the group consisting of hydrogen, $C_{1-6}$ alkyl, haloC$_{1-6}$ alkyl, $C_{3-10}$ cycloalkyl, $C_{6-10}$ aryl, and ($C_{6-10}$ aryl) $C_{1-6}$ alkyl; and X and Y each are —OR$^4$.

5. The pharmaceutical composition of claim 4, wherein $Z^1$ is selected from the group consisting of hydrogen, $C_{1-6}$ alkyl and haloC$_{1-6}$ alkyl; and each $R^4$ independently is selected from the group consisting of hydrogen, $C_{6-10}$ aryl and $C_{6-10}$ aryl alkyl.

6. The pharmaceutical composition of claim 4, wherein $Z^1$ is hydrogen and each $R^4$ independently is hydrogen or $C_{6-10}$ aryl alkyl.

7. The pharmaceutical composition of claim 4, wherein each $R^4$ is hydrogen.

8. The pharmaceutical composition of claim 1, wherein the compound has the structure of formula I-b:

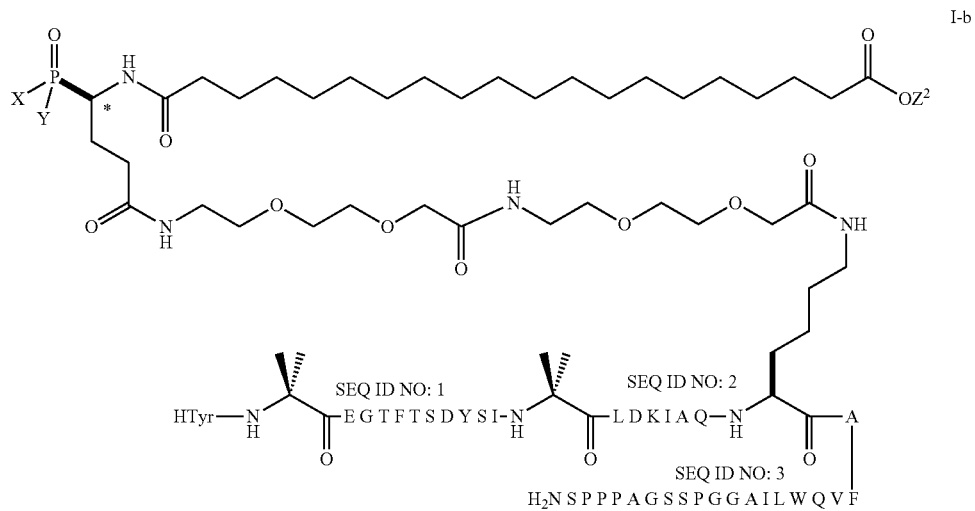

or a pharmaceutically acceptable salt thereof.

9. The pharmaceutical composition of claim 8, wherein $Z^2$ is selected from the group consisting of hydrogen, $C_{1-6}$ alkyl, halo$C_{1-6}$ alkyl, $C_{3-10}$ cycloalkyl, $C_{6-10}$ aryl, and ($C_{6-10}$ aryl) $C_{1-6}$ alkyl; and X and Y each are —$OR^4$.

10. The pharmaceutical composition of claim 9, wherein $Z^2$ is selected from the group consisting of hydrogen, halo$C_{1-6}$ alkyl and $C_{1-6}$ alkyl; and each $R^4$ independently is selected from the group consisting of hydrogen, $C_{6-10}$ aryl and $C_{6-10}$ aryl alkyl.

11. The pharmaceutical composition of claim 9, wherein $Z^2$ is hydrogen and each $R^4$ is hydrogen or $C_{6-10}$ aryl alkyl.

12. The pharmaceutical composition of claim 9, wherein each $R^4$ is hydrogen.

13. The pharmaceutical composition of claim 1, wherein the compound has the structure of formula I-c:

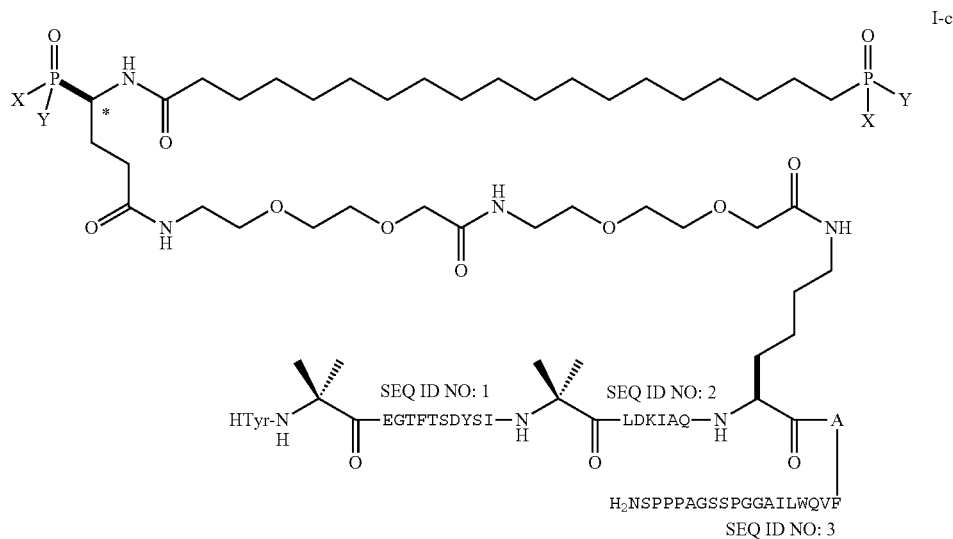

or a pharmaceutically acceptable salt thereof.

14. The pharmaceutical composition of claim 13, wherein X and Y each are —OR⁴.

15. The pharmaceutical composition of claim 14, wherein each R⁴ is independently selected from the group consisting of hydrogen, $C_{6-10}$ aryl and $C_{6-10}$ aryl alkyl.

16. A pharmaceutical composition comprising a pharmaceutically acceptable excipient and a compound having the structure selected from the group consisting of:

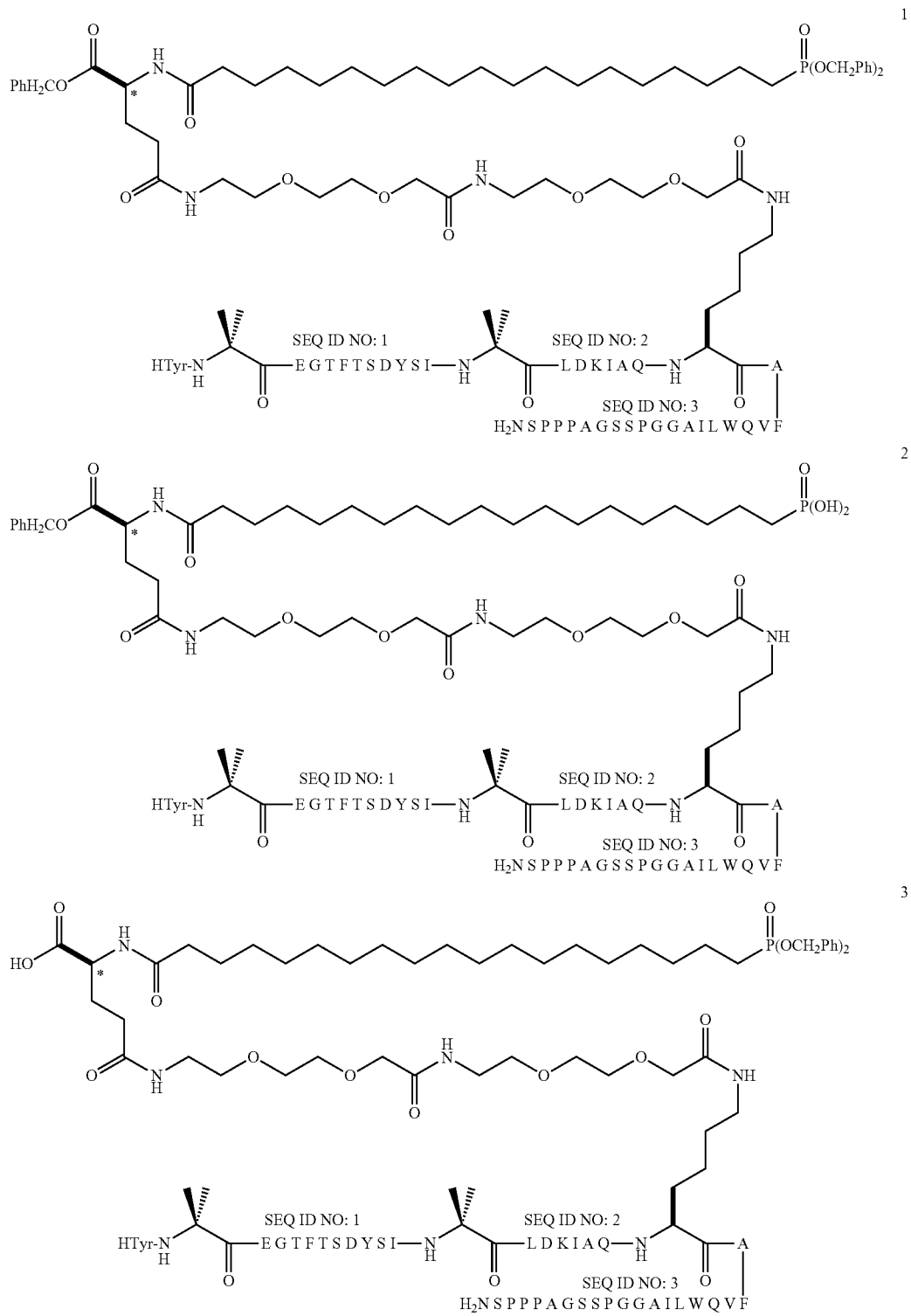

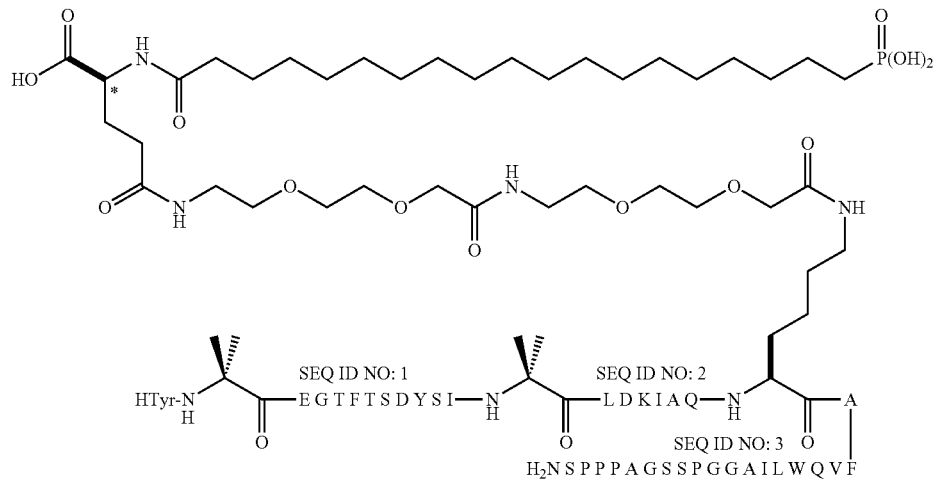
4
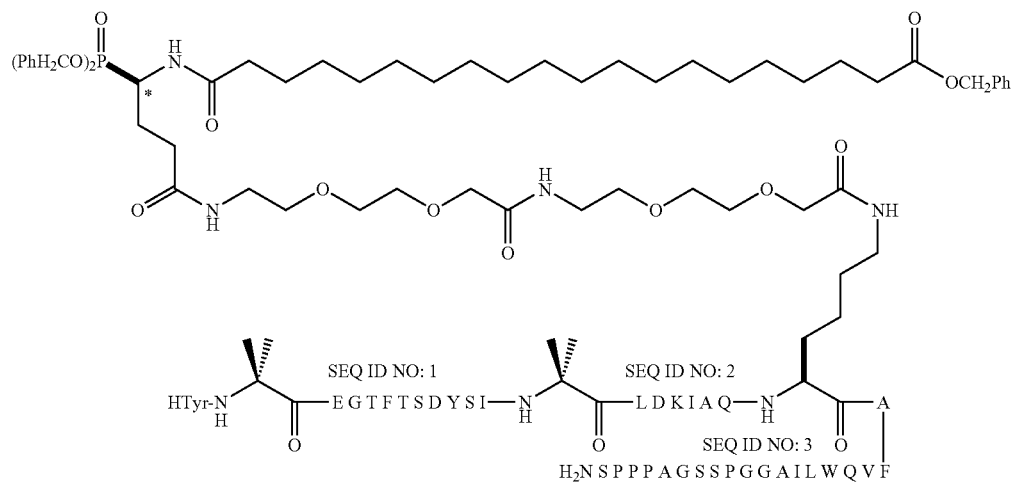
5
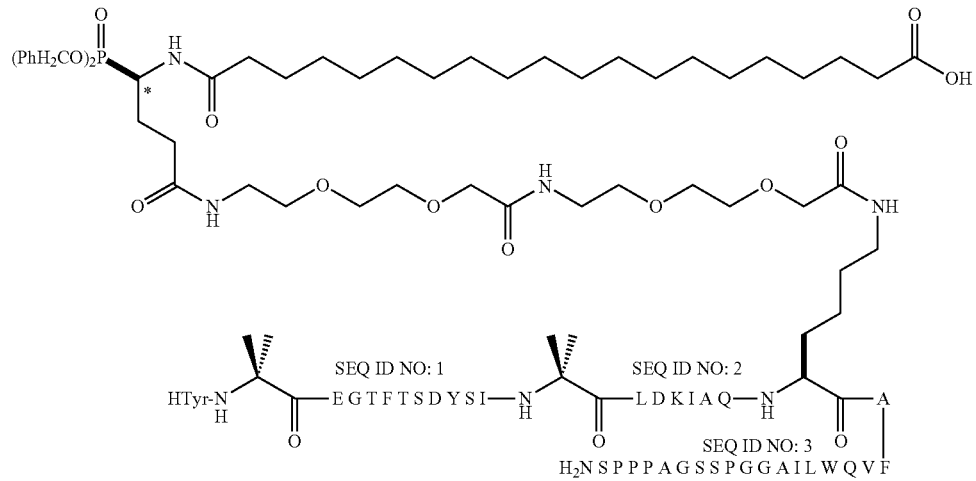
6

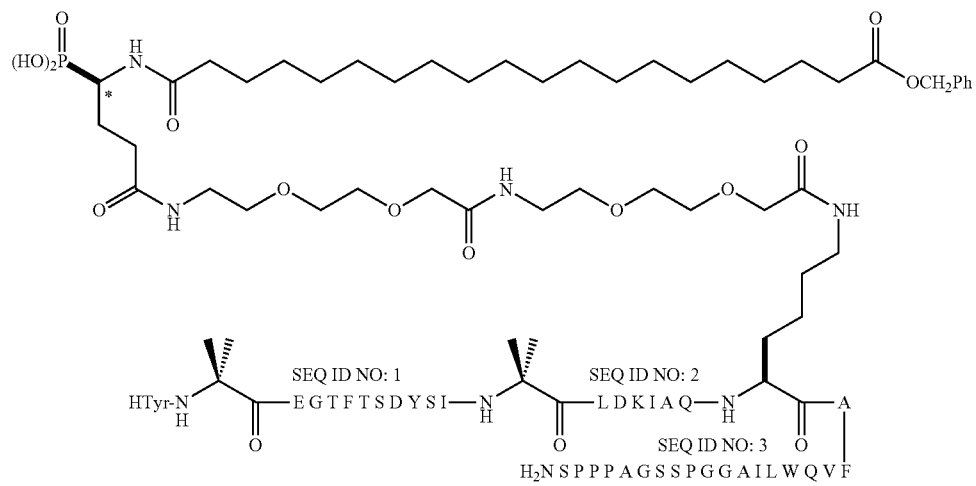
7
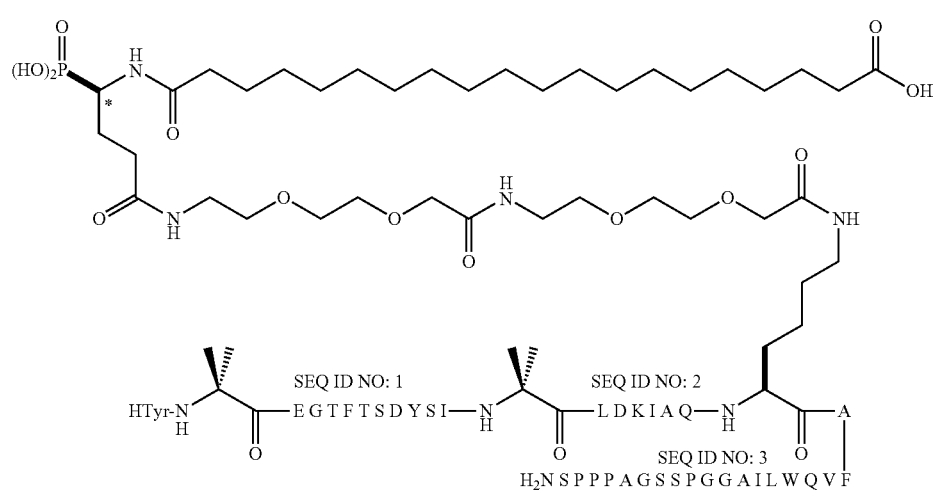
8
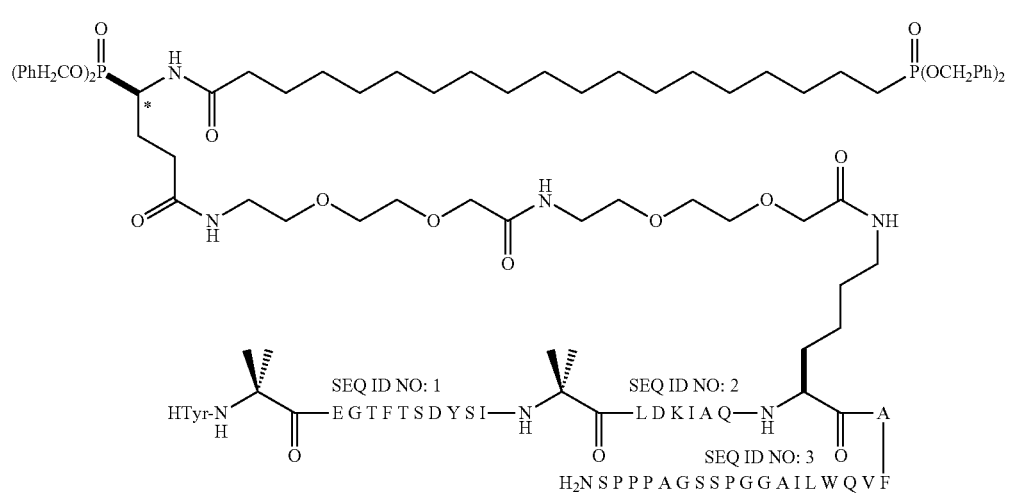
9

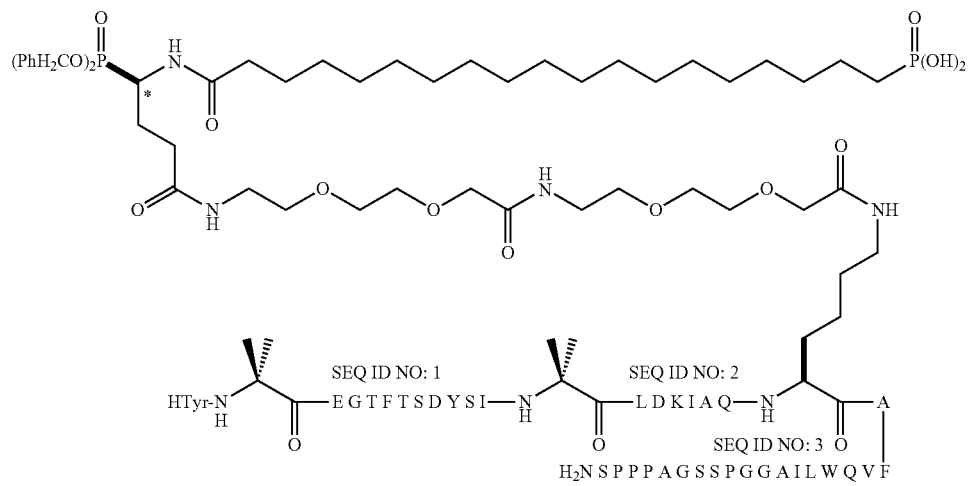
10
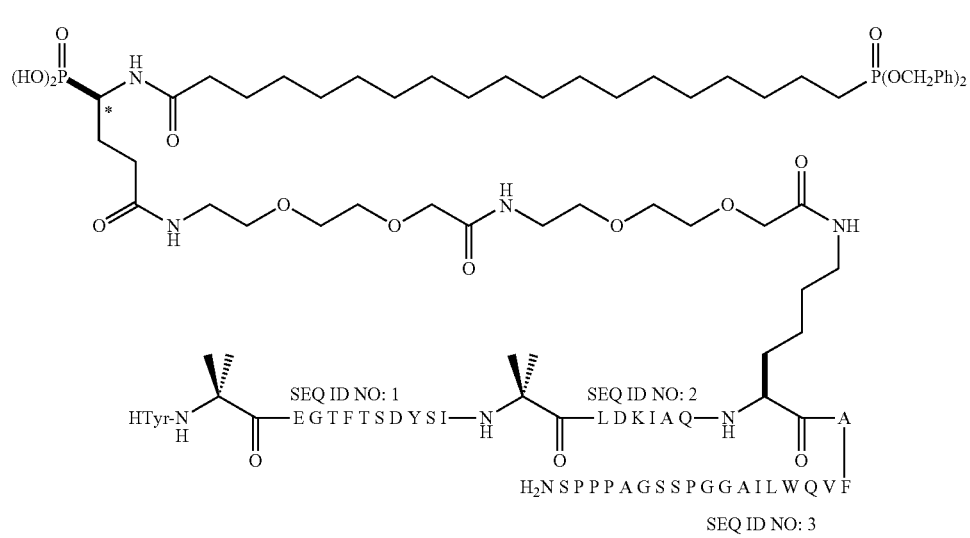
11
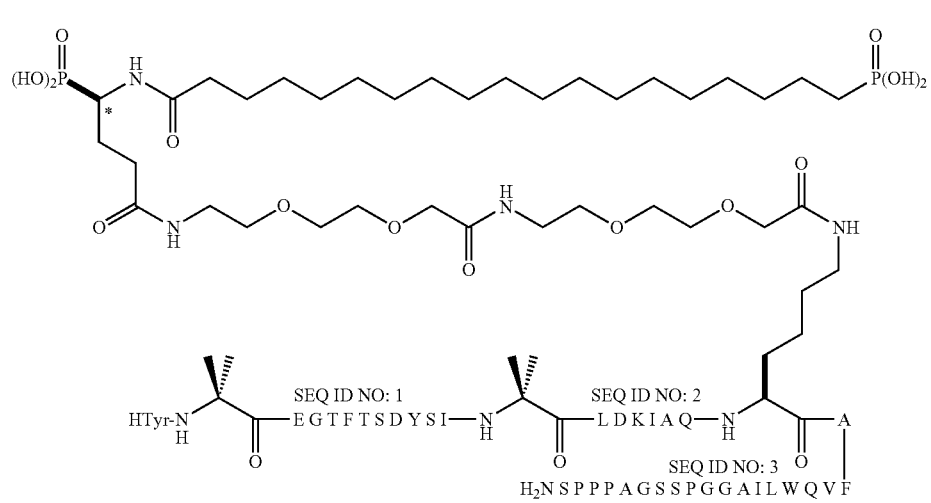
12
and pharmaceutically acceptable salts thereof,
wherein "*" indicates a chiral carbon with "S" configuration or "R" configuration.

17. The pharmaceutical composition of claim 16 comprising a compound having the structure:
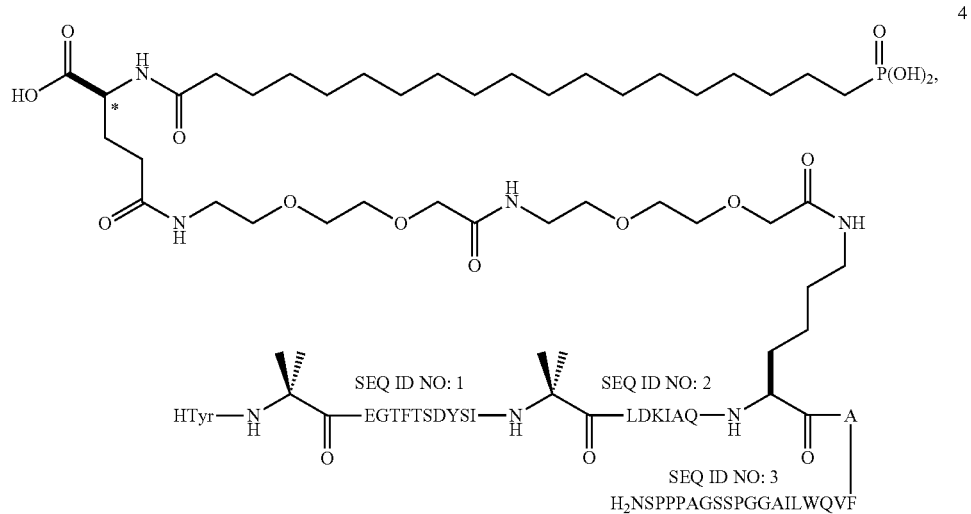
or a pharmaceutically acceptable salt thereof.
18. The pharmaceutical composition of claim 16 comprising a compound having the structure:
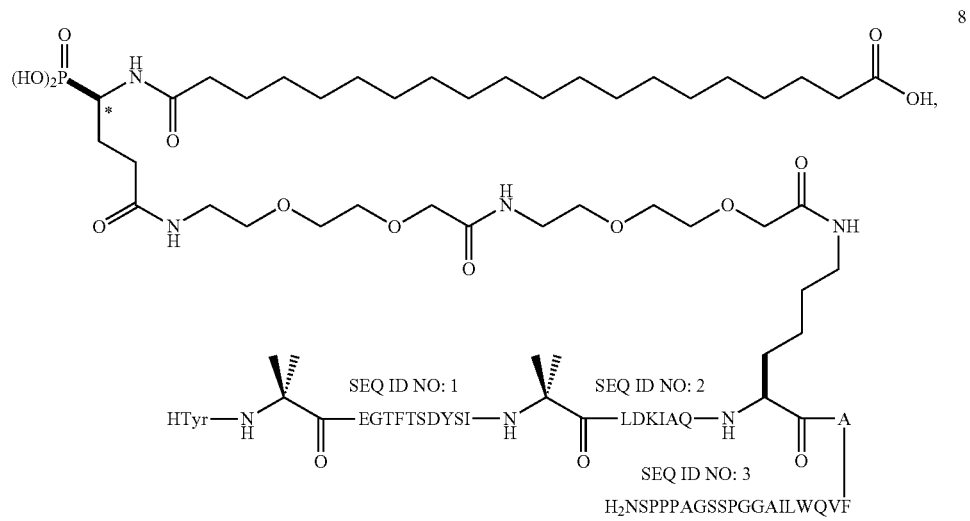
or a pharmaceutically acceptable salt thereof.

19. The pharmaceutical composition of claim 16 comprising a compound having the structure:

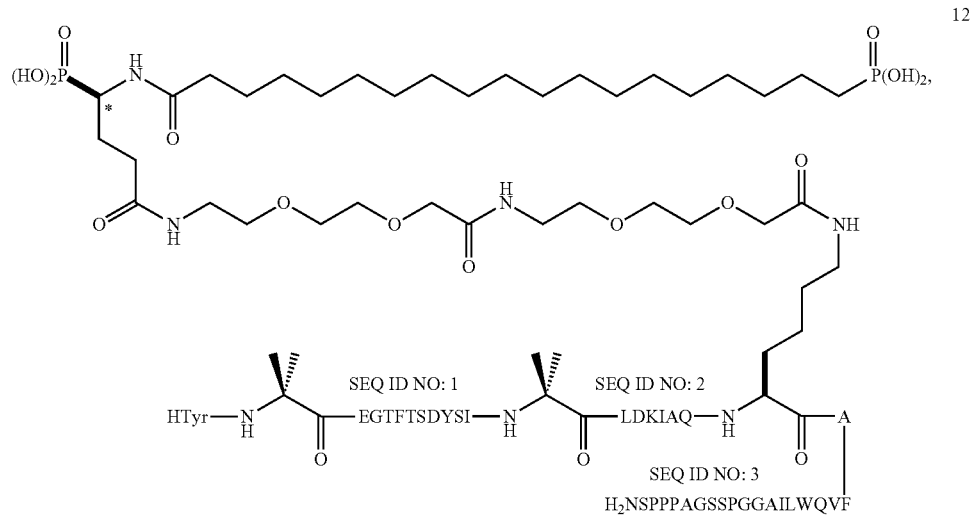

or a pharmaceutically acceptable salt thereof.

20. The pharmaceutical composition of claim 16 comprising a compound having the structure:

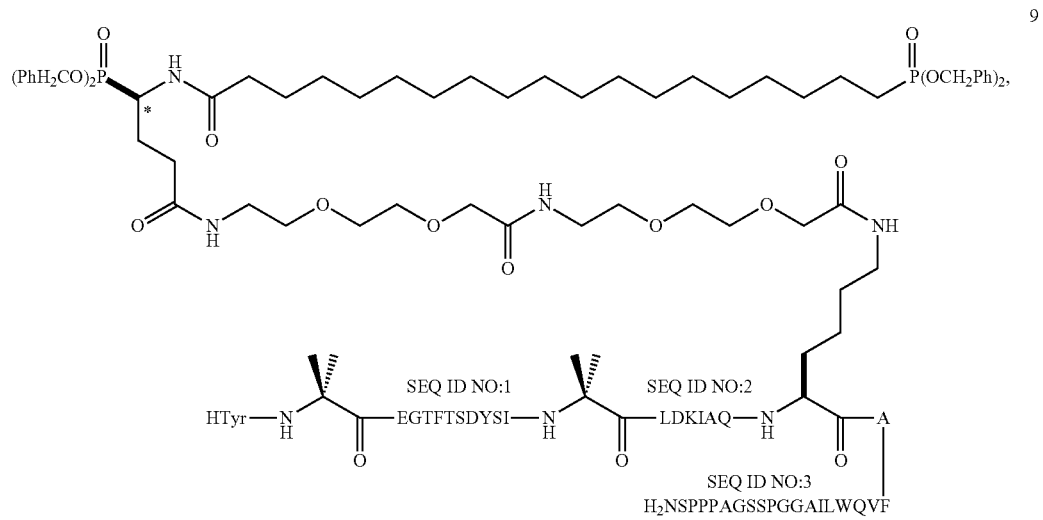

or a pharmaceutically acceptable salt thereof.

21. The pharmaceutical composition of claim 1, wherein "*" indicates a chiral carbon with "S" configuration.

22. The pharmaceutical composition of claim 1, wherein "*" indicates a chiral carbon with "R" configuration.

* * * * *

```
                           SEQUENCE LISTING

Sequence total quantity: 4
SEQ ID NO: 1              moltype = AA  length = 10
FEATURE                   Location/Qualifiers
source                    1..10
                          mol_type = protein
                          organism = synthetic construct
SEQUENCE: 1
EGTFTSDYSI                                                              10

SEQ ID NO: 2              moltype = AA  length = 6
FEATURE                   Location/Qualifiers
source                    1..6
                          mol_type = protein
                          organism = synthetic construct
SEQUENCE: 2
LDKIAQ                                                                   6

SEQ ID NO: 3              moltype = AA  length = 19
FEATURE                   Location/Qualifiers
source                    1..19
                          mol_type = protein
                          organism = synthetic construct
SEQUENCE: 3
SPPPAGSSPG GAILWQVFA                                                    19

SEQ ID NO: 4              moltype = AA  length = 19
FEATURE                   Location/Qualifiers
source                    1..19
                          mol_type = protein
                          organism = synthetic construct
SEQUENCE: 4
AFVQWLIAGG PSSGAPPPS                                                    19
```